(12) United States Patent
Lalonde et al.

(10) Patent No.: US 12,226,140 B2
(45) Date of Patent: *Feb. 18, 2025

(54) SOFT BALLOON DEVICE AND SYSTEM

(71) Applicant: Medtronic CryoCath LP, Toronto (CA)

(72) Inventors: Jean-Pierre Lalonde, Candiac (CA); Scott A. Hareland, Lino Lakes, MN (US); Jay L. Kelley, Encinitas, CA (US); Rachid Mahrouche, Cote St-Luc (CA); Wlodzimierz Sadzynski, Chateauguay (CA); Megan M. Schmidt, Minneapolis, MN (US); Bertin Simeon, Laval (CA); Vladimir Tzonev, Kirkland (CA)

(73) Assignee: Medtronic CryoCath LP, Toronto (CA)

( * ) Notice: Subject to any disclaimer, the term of this patent is extended or adjusted under 35 U.S.C. 154(b) by 877 days.

This patent is subject to a terminal disclaimer.

(21) Appl. No.: 17/375,215

(22) Filed: Jul. 14, 2021

(65) Prior Publication Data
US 2021/0338303 A1  Nov. 4, 2021

Related U.S. Application Data

(63) Continuation of application No. 15/969,280, filed on May 2, 2018, now Pat. No. 11,090,101.

(51) Int. Cl.
*A61B 18/02* (2006.01)
*A61B 18/00* (2006.01)
*A61M 25/10* (2013.01)

(52) U.S. Cl.
CPC .... *A61B 18/02* (2013.01); *A61B 2018/00244* (2013.01); *A61B 2018/00404* (2013.01);
(Continued)

(58) Field of Classification Search
CPC .............. A61M 2025/0079; A61M 2025/0175
See application file for complete search history.

(56) References Cited

U.S. PATENT DOCUMENTS 4,955,375 A   9/1990  Martinez
4,969,470 A  11/1990  Mohl et al.
(Continued)

OTHER PUBLICATIONS

International Search Report and Written Opinion dated Jun. 18, 2019, for corresponding International Application No. PCT/CA2019/050373 International Filing Date: Mar. 27, 2019 consisting of 11-pages.

(Continued)

*Primary Examiner* — Ronald Hupczey, Jr.
(74) *Attorney, Agent, or Firm* — Michael Best & Friedrich LLP

(57) ABSTRACT

A device, system, and method for performing a variety of treatment procedures safely with a single treatment device. For example, a system is provided that includes a treatment device with a highly conformable balloon that is inflated at a constant pressure and that remains "soft" during use, which enhances balloon-tissue contact, treatment efficacy, and patient safety. In one embodiment, a system for ablating tissue comprises: a treatment device including a highly conformable balloon; a control unit including a fluid supply reservoir in fluid communication with the highly conformable balloon, the control unit being configured to deliver fluid from the fluid supply reservoir to the highly conformable balloon such that the highly conformable balloon is maintained at a balloon pressure of between 0.2 psig and 3.0 psig.

20 Claims, 16 Drawing Sheets

(52) U.S. Cl.
CPC ............... *A61B 2018/00577* (2013.01); *A61B 2018/00744* (2013.01); *A61B 2018/00773* (2013.01); *A61B 2018/0212* (2013.01); *A61M 25/1002* (2013.01); *A61M 25/10184* (2013.11); *A61M 25/10185* (2013.11)

(56) References Cited

U.S. PATENT DOCUMENTS

| | | | |
|---|---|---|---|
| 6,032,673 | A | 3/2000 | Savage et al. |
| 6,179,854 | B1 | 1/2001 | Nash et al. |
| 6,652,515 | B1 | 11/2003 | Maguire et al. |
| 9,086,303 | B2 | 7/2015 | Wiklund |
| 9,625,103 | B2 | 4/2017 | Zimmer et al. |
| 9,737,693 | B2 | 8/2017 | Helkowski et al. |
| 9,757,535 | B2 | 9/2017 | Rajagopalan et al. |
| 9,931,152 | B2 | 4/2018 | Wittenberger et al. |
| 10,189,513 | B2 | 1/2019 | Heil |
| 11,090,101 | B2 * | 8/2021 | Lalonde ................. A61B 18/02 |
| 2009/0299356 | A1 | 12/2009 | Watson |
| 2010/0049184 | A1 | 2/2010 | George et al. |
| 2010/0114269 | A1 | 5/2010 | Wittenberger et al. |
| 2010/0211056 | A1 | 8/2010 | Mihalik et al. |
| 2011/0082450 | A1 | 4/2011 | Melsky et al. |
| 2011/0257523 | A1 | 10/2011 | Hastings et al. |
| 2012/0265188 | A1 | 10/2012 | Buchbinder et al. |
| 2013/0165736 | A1 | 6/2013 | Mohl et al. |
| 2014/0066929 | A1 | 3/2014 | Mark et al. |
| 2014/0276198 | A1 | 9/2014 | Dunung et al. |
| 2015/0105764 | A1 | 4/2015 | Rizq et al. |
| 2015/0196740 | A1 | 7/2015 | Mallin et al. |
| 2015/0265812 | A1 | 9/2015 | Lalonde |
| 2015/0374436 | A1 | 12/2015 | Subramaniam et al. |
| 2016/0015444 | A1 | 1/2016 | Wittenberger |
| 2016/0045098 | A1 | 2/2016 | Tsubouchi |
| 2018/0236203 | A1 | 8/2018 | Franklin et al. |
| 2019/0314109 | A1 | 10/2019 | Brucker et al. |

OTHER PUBLICATIONS

Canadian Patent Office Examination Report for Application No. 3,091,706 dated Jan. 12, 2023 (5 pages).
European Patent Office Exam Report for Application No. 19796108.9 dated Apr. 14, 2023 (4 pages).
European Patent Office, Supplementary European Search Report, for corresponding EP Application No. EP 19796108, dated Jan. 5, 2022, 6 pages.
Canadian Patent Office Action for Application No. 3,091,706 dated Mar. 22, 2022 (4 pages).
Chinese Patent Office Notice on the First Office Action for Application No. 201980026075.8 dated Jan. 6, 2024 (17 pages including English translation).
China National Intellectual Property Administration Second Office Action for Application No. 201980026075.8 dated Jul. 19, 2024 (7 pages including English translation).

* cited by examiner

SOFT BALLOON DEVICE AND SYSTEM

CROSS-REFERENCE TO RELATED APPLICATION

This application is a continuation of U.S. application Ser. No. 15/969,280, filed May 2, 2018, now U.S. Pat. No. 11,090,101, the entirety of which is incorporated herein by reference.

STATEMENT REGARDING FEDERALLY SPONSORED RESEARCH OR DEVELOPMENT n/a

TECHNICAL FIELD

The present invention relates to a device, system, and method for performing a variety of treatment procedures safely with a single treatment device. For example, a system is provided that includes a treatment device with a highly conformable balloon that is inflated at a constant pressure and that remains "soft" during use, which enhances balloon-tissue contact, treatment efficacy, and patient safety.

BACKGROUND

Cardiac arrhythmia, a group of disorders in which the heart's normal rhythm is disrupted, affects millions of people. Certain types of cardiac arrhythmias, including ventricular tachycardia and atrial fibrillation, may be treated using one or more energy modalities, such as cryoablation, either endocardially or epicardially.

The effectiveness of an ablation procedure may largely depend on the quality of contact between the treatment element of the medical device and the cardiac tissue. Procedures such as pulmonary vein isolation (PVI) are commonly used to treat cardiac arrhythmias such as atrial fibrillation. In such a procedure, the treatment element, such as a cryoballoon, may be positioned at the pulmonary vein ostium in order to create a circumferential lesion surrounding the ostium. However, the success of this procedure depends largely on the quality of the lesion(s) created during the procedure and whether the cryoballoon has completely occluded the pulmonary vein. For example, a complete circumferential lesion is produced only when the cryoballoon has completely occluded the pulmonary vein. Incomplete occlusion, on the other hand, allows blood to flow from the pulmonary vein being treated, past the cryoballoon, and into the left atrium of the heart. This flow of warm blood may prevent the cryoballoon from reaching temperatures low enough to create permanent lesions in the targeted tissue. The creation of reversible lesions may not be sufficient to achieve electrical isolation and, as a result, the cardiac condition may be likely to reoccur.

When performing PVI, it also may be difficult to prevent the treatment element from moving too deep within the pulmonary vein when applying sufficient pressure through the device elongate body to ensure adequate contact between the treatment element and the pulmonary vein ostium. Ablating tissue within the pulmonary vein may lead to complications such as cardiac tamponade, in which the pericardial sac surrounding the heart fills will blood, and pulmonary vein stenosis.

Additionally, treatment elements of different sizes, shapes, and configurations may all be required in a single ablation procedure. For example, an ablation procedure may involve PVI and linear ablation patterns. To achieve this, a physician may employ several different catheters having variations in the geometry and/or dimensions of the treatment element in order to produce the desired ablation pattern. Each device may have a unique geometry for creating a specific lesion pattern, with the multiple catheters being sequentially removed and replaced to create the desired lesions. However, exchanging the various devices during a procedure can cause inaccuracies or movement in the placement and location of the distal tip with respect to the targeted tissue, and may further add to the time required to perform the procedure and may increase the risk of patient injury and discomfort. Even if a single device includes a treatment element that is transitionable between configurations to provide a number of different ablation patterns, it may be physically challenging to transition the treatment element without displacing the device from the treatment site.

SUMMARY

The present invention advantageously provides a device, system, and method for performing a variety of treatment procedures safely with a single treatment device. For example, a system is provided that includes a treatment device with a highly conformable balloon that is inflated at a constant pressure and that remains "soft" during use, which enhances balloon-tissue contact, treatment efficacy, and patient safety.

In one embodiment, a system for ablating tissue comprises: a treatment device including a highly conformable balloon; and a control unit including a fluid supply reservoir in fluid communication with the highly conformable balloon, the control unit being configured to deliver fluid from the fluid supply reservoir to the highly conformable balloon such that the highly conformable balloon is maintained at a balloon pressure of between 0.2 psig and 3.0 psig.

In one aspect of the embodiment, the control unit is configured to maintain the balloon pressure between 0.2 psig and 3.0 psig during inflation of the highly conformable balloon.

In one aspect of the embodiment, the control unit is configured to maintain the balloon pressure between 0.2 psig and 3.0 psig during ablation of tissue.

In one aspect of the embodiment, the system further comprises: a vacuum source; a fluid delivery conduit between the fluid supply reservoir and the highly conformable balloon; and a fluid return conduit between the highly conformable balloon and the vacuum source.

In one aspect of the embodiment, the system further comprises: a flow control valve in fluid communication with the fluid delivery conduit; and a pressure control valve in fluid communication with the fluid return conduit, the control unit being configured to selectively adjust the flow control valve and the pressure control valve to maintain the balloon pressure between 0.2 psig and 3.0 psig.

In one aspect of the embodiment, the system further comprises: a Pitot tube at least partially disposed within the highly conformable balloon; and a pressure sensor in communication with the Pitot tube. In one aspect of the embodiment, the control unit is configured to determine the balloon pressure based on a pressure measurement recorded by the pressure sensor. In one aspect of the embodiment, the control unit is configured to determine a static pressure within the highly conformable balloon based on a recorded stagnation pressure within the highly conformable balloon.

In one aspect of the embodiment, the treatment element further includes a pressure sensor within the highly conformable balloon, the pressure sensor being in communication with the control unit and being configured to record pressure signals generated by a heartbeat, the control unit being configured to determine an occlusion status of the highly conformable balloon based on the pressure signals recorded by the pressure sensor.

In one aspect of the embodiment, the treatment device further includes: an elongate body having a proximal portion and a distal portion; a shaft slidably disposed within the elongate body; a handle, the handle being fixedly coupled to the elongate body proximal portion; and an actuator element being in mechanical communication with the shaft and at least partially disposed within the handle, the actuator element and the shaft being freely movable with respect to the handle and the elongate body. In one aspect of the embodiment, the shaft has a proximal portion and a distal portion, the highly conformable balloon having: a proximal neck coupled to the elongate body distal portion; and a distal neck coupled to the shaft distal portion, retraction of the actuator element from an initial position transitioning the highly conformable balloon between a first configuration and a second configuration and extension of the actuator element from the initial position transitioning the highly conformable balloon between the first configuration and a third configuration.

In one aspect of the embodiment, the first configuration is an at least substantially round configuration. In one aspect of the embodiment, the highly conformable balloon is inflatable to a first outer diameter when in the first configuration and is further inflatable to a second outer diameter when in the first configuration. In one aspect of the embodiment, the first outer diameter is approximately 23 mm and the second outer diameter is approximately 36 mm.

In one aspect of the embodiment, the second configuration is a toroidal configuration.

In one aspect of the embodiment, the third configuration is an elongated configuration.

In one embodiment, a system for ablating tissue comprises: a treatment device including: an elongate body having a distal portion and a proximal portion; a shaft slidably disposed within the elongate body, the shaft having a proximal portion and a distal portion; a highly conformable balloon having a distal neck and a proximal neck, the distal neck being coupled to the shaft distal portion and the proximal neck being coupled to the elongate body distal portion; a control unit including: processing circuitry; a coolant supply reservoir; and a vacuum source; a fluid delivery conduit between the coolant supply reservoir and the highly conformable balloon; and a fluid return conduit between the highly conformable balloon and the vacuum source, the processing circuitry being configured to adjust a flow of coolant through the fluid delivery conduit and the fluid return conduit to maintain the highly conformable balloon at a balloon pressure of between 0.2 psig and 3.0 psig during both an inflation phase and an ablation phase, the processing circuitry being further configured to control the balloon pressure independently of a flow rate of coolant from the coolant supply reservoir.

In one aspect of the embodiment, the system further comprises: a flow control valve in fluid communication with the fluid delivery conduit; and a pressure control valve in fluid communication with the fluid return conduit, the processing circuitry being configured to control the flow control valve and the pressure control valve and the vacuum source to maintain the balloon pressure at between 0.2 psig and 3.0 psig.

In one embodiment, a method of performing a medical procedure comprises: selecting a desired inflated size of a balloon of a treatment device; delivering a fluid to the balloon and withdrawing coolant from the balloon such that the balloon is inflated to the desired size and has a pressure of between 0.2 psig and 3.0 psig; delivering a coolant to the balloon at a flow rate and maintaining the balloon at the pressure of between 0.2 psig and 3.0 psig, the pressure being controlled independently of the flow rate of the coolant, delivery of the coolant to the balloon reducing a temperature of the balloon to a temperature sufficient to cryoablate tissue; positioning the treatment device such that the balloon is in contact with an area of targeted tissue; and cryoablating the area of targeted tissue with the balloon.

In one aspect of the embodiment, the method further comprises: continuously monitoring a pressure within the balloon; and adjusting a flow of the coolant to the balloon and from the balloon by adjusting at least one a flow control valve and a pressure control valve, adjusting the at least one of the flow control valve and the pressure control valve being independent of adjusting the flow rate of the coolant.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The devices, systems, and methods disclosed herein are for treating an area of tissue, such as performing pulmonary vein isolation, spot ablation, and/or linear ablation with a single treatment device. For example, a system is provided that includes a treatment device with a highly conformable balloon that is inflated at a constant pressure and that remains "soft" during use, which enhances balloon-tissue contact, treatment efficacy, and patient safety.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
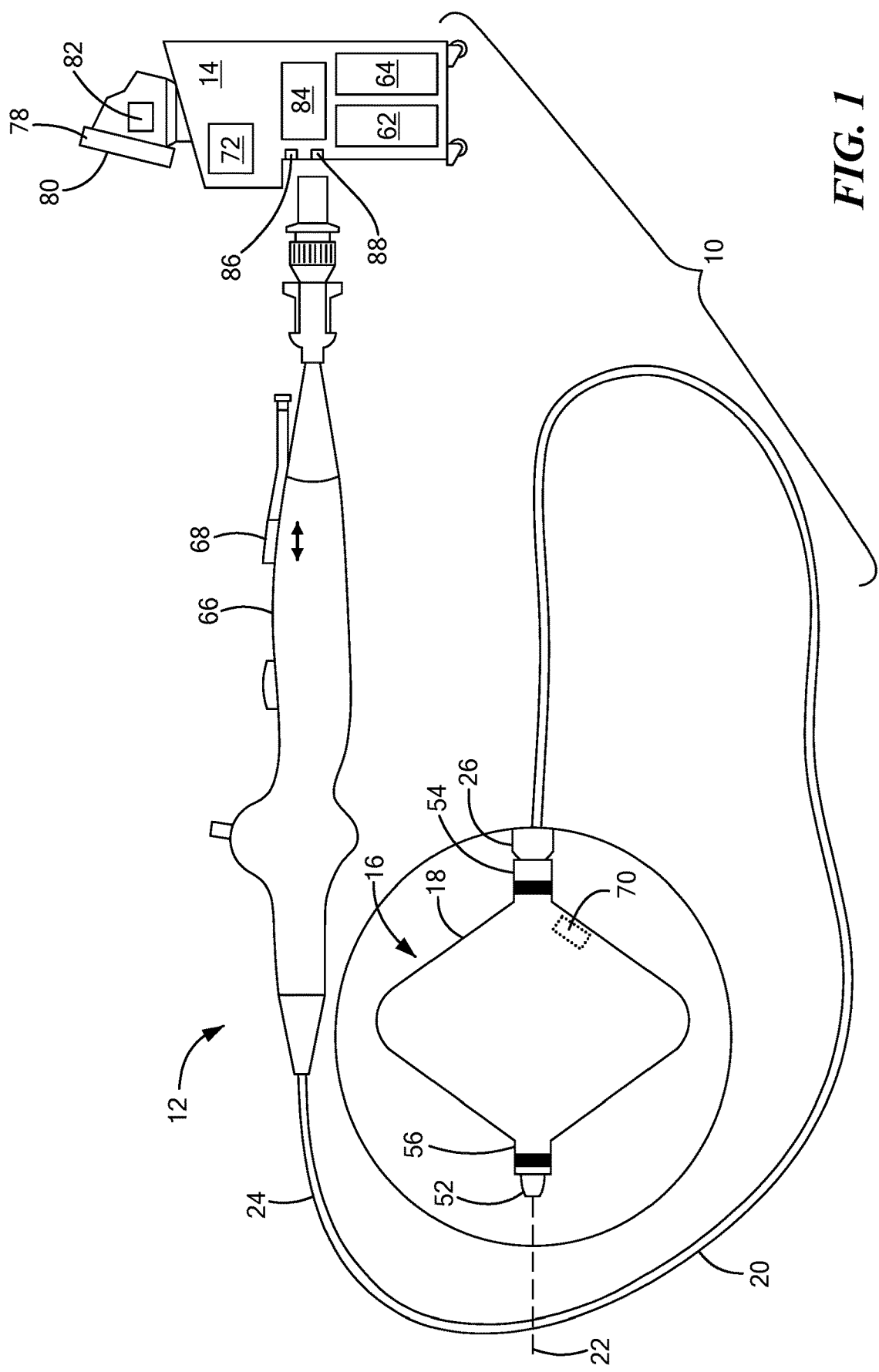
FIG. 1 shows an exemplary medical system including a medical device having a highly conformable balloon.

Referring now to the drawing figures in which like reference designations refer to like elements, an embodiment of a medical system is shown in FIG. 1, generally designated as "10." The device and system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

One embodiment of the medical system 10 may generally include a treatment device 12 in communication with a control unit 14. The treatment device 12 may include one or more diagnostic or treatment elements 16 for energetic or other therapeutic interaction between the treatment device 12 and a treatment site (which may also be referred to as an area of targeted tissue). The treatment element(s) 16 may deliver, for example, cryogenic therapy, and may further be configured to deliver radiofrequency energy, or otherwise for energetic transfer with a tissue area in proximity to the area(s) of targeted tissue, including cardiac tissue. In particular, the one or more treatment elements 16 may be configured to reduce the temperature of adjacent tissue in order to perform cryotreatment and/or cryoablation. For example, the treatment element(s) 16 may include one or more balloons 18 (as shown in FIG. 1) within which a cryogenic coolant may be circulated in order to reduce the temperature of the balloon. As is discussed in more detail below, the balloon(s) 18 are configured to be "soft" (that is, easily deformable and/or conformable to an area of targeted tissue) when fully inflated. Additionally, the treatment element(s) 16 may include other thermally and/or electrically-conductive components, such as one or more electrodes in communication with the control unit 14.

Figure 2:
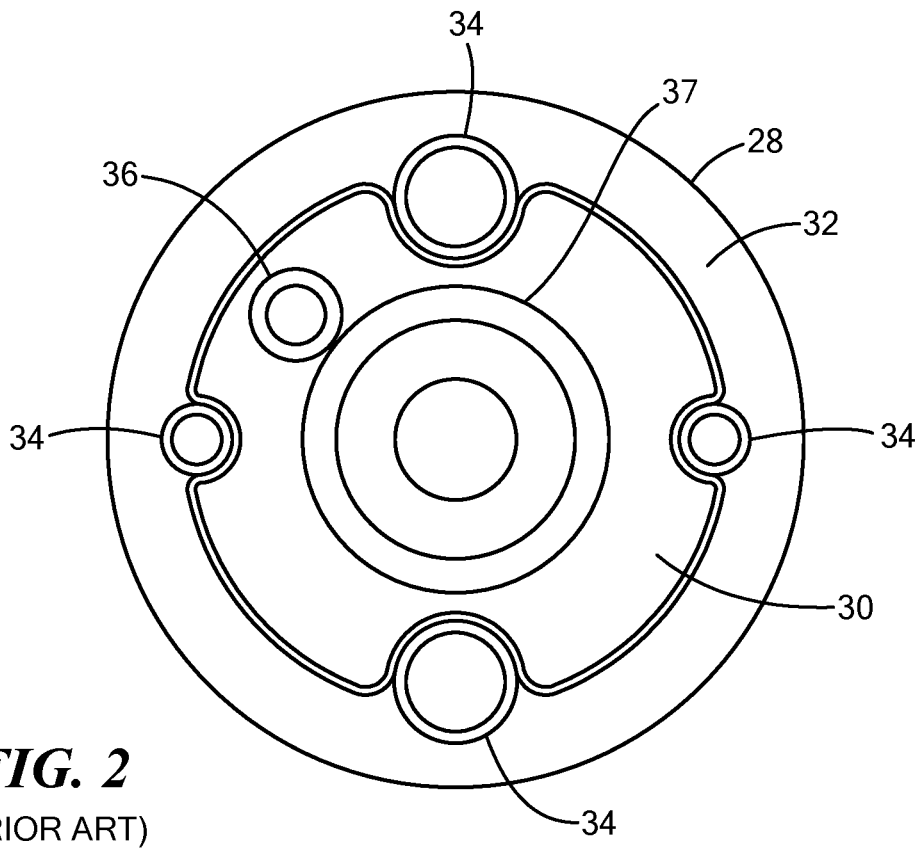
FIG. 2 shows a cross-sectional view of an elongate body of a currently known medical device.
Figure 3:
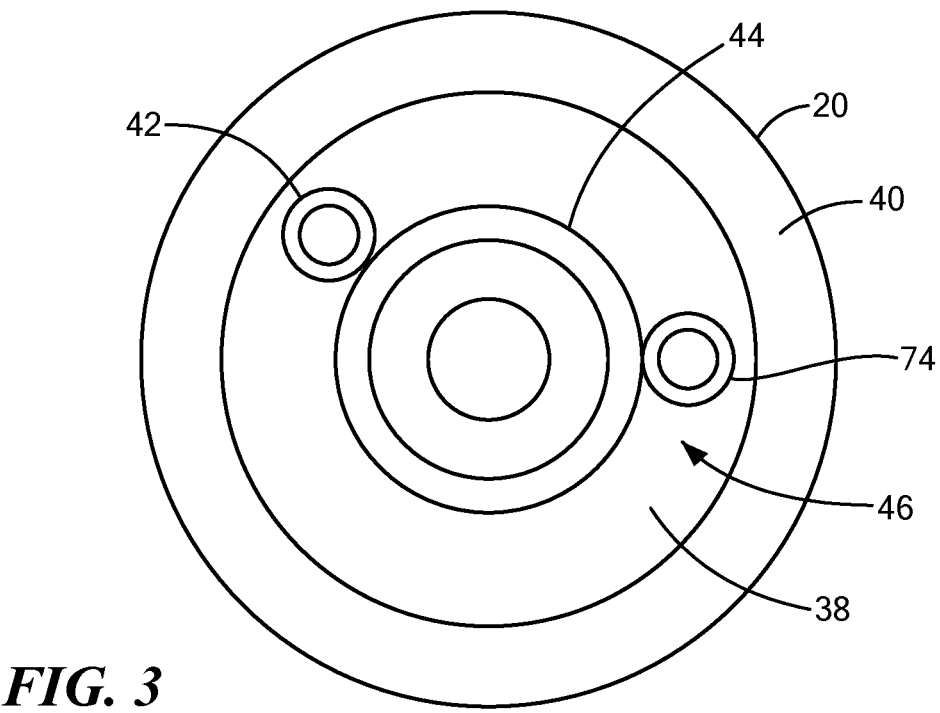
FIG. 3 shows a cross-sectional view of an elongate body of a medical device disclosed herein.

In one embodiment, the treatment device 12 includes an elongate body 20 sized and configured to be passable through a patient's vasculature and/or positionable proximate to a tissue region for diagnosis or treatment, such as a catheter, sheath, or intravascular introducer. For example, the elongate body 20 may have an outer diameter of 11 Fr. The elongate body 20 defines a longitudinal axis 22, a proximal portion 24, and a distal portion 26, and may further include one or more lumens disposed within the elongate body 20 that provide mechanical, electrical, and/or fluid communication between the proximal portion 24 of the elongate body 20 and the distal portion 26 of the elongate body 20. In currently known devices, the elongate body 28 may include a central lumen 30, an outer wall 32 with a plurality of smaller lumens 34 therein that extend into the central lumen 30, a fluid delivery conduit 36, and a guidewire lumen 37 (for example, as shown in FIG. 2). The area of the central lumen 30 between the outer wall 32 (and plurality of smaller lumens 34) and the guidewire lumen 37 defines the fluid return conduit. However, extension of the plurality of smaller lumens 34 into the central lumen 30 restricts the fluid return conduit. In contrast, the treatment device 12 disclosed herein does not include the plurality of smaller lumens 34, and therefore provides a larger fluid return conduit that is capable of more rapidly evacuating fluid from the balloon 18. For example, as shown in FIG. 3, the elongate body 20 includes a central lumen 38, an outer wall 40, a fluid delivery conduit 42, and, optionally, a guidewire lumen 44. The area of the central lumen 38 between the outer wall 40 and the guidewire lumen 44 defines the fluid return conduit 46. In one embodiment, the configuration shown in FIG. 3 can provide an increase of over 30% in the volume of the fluid return conduit as compared to currently known designs. Additionally, the larger volume of the fluid return conduit lowers the pressure drop within the elongate body 20.

In one embodiment, the treatment device 12 further includes a shaft 48 that is slidably disposed within the elongate body 20. For example, the shaft 48 is a flexible linear shaft that is longitudinally movable within a lumen (for example, the central lumen 38 or the guidewire lumen 44) of the elongate body 20. Further, the shaft 48 includes a proximal portion (not shown) and a distal portion 50 with a distal tip 52. Movement of the shaft 48 may affect the shape and configuration of the balloon 18. For example, the shaft 48 may be fully advanced when the balloon 18 is deflated and in a delivery (or first) configuration wherein the balloon 18 has a minimum diameter suitable, for example, for retraction of the treatment device 12 within a sheath for delivery to and removal from the treatment site. Conversely, when the balloon 18 is inflated and in a treatment (or second) configuration, the shaft 48 may be advanced or retracted over a distance that affects the size and configuration of the inflated balloon 18, as is discussed in greater detail herein. Further, the shaft 48 may include a guidewire lumen through which a sensing device, mapping device, guidewire, or other system component may be located and extended from the distal end of the treatment device 12.

As noted above, in one embodiment the one or more treatment elements 16 includes a single expandable element, such as the balloon 18 shown in the figures. However, it will be understood that the treatment device 12 may include more than one treatment element 16, including expandable and/or non-expandable treatment elements (for example, an interior balloon surrounded by an exterior balloon), electrodes, or other suitable energy exchange structures or components. In the embodiment shown in FIG. 1, the treatment element 16 includes a balloon 18, such as a cryoballoon, that has a proximal neck 54 that is coupled to the elongate body distal portion 26 and a distal neck 56 that is coupled to the shaft distal portion 50. In one embodiment, the distal neck 56 is coupled to the shaft distal tip 52. The proximal 54 and distal 56 necks of the balloon 18 may be coupled to the elongate body 20 and shaft 48, respectively, using any suitable means, such as with adhesives, chemical bonding, laser welding, with one or more mechanical coupling elements, or the like. Further, the balloon 18 is a compliant or highly compliant balloon composed of one or more materials such as polyurethane, polyolefin copolymer (POC), or other material that allows the balloon to be "soft" (that is, easily deformable and/or conformable to an area of targeted tissue) when fully inflated. This compliant or highly compliant balloon 18 is referred to herein as a "highly conformable balloon." Additionally, the balloon 18 may be inflatable to a first outer diameter (for example, of approximately 23 mm) and further inflatable to a second outer diameter (for example, of approximately 36 mm), at an inflation pressure of between 0.2 psig and 3.0 psig, which pressure is also the pressure of the balloon 18 when the balloon 18 is used for an ablation procedure. In contrast, currently known balloons are inflated at a pressure of approximately 2 psig, with an ablation pressure of 17.5 psig.

The treatment device 12 includes one or more nozzles, orifices, or other fluid delivery elements 58 for delivering fluid to the interior chamber 60 of the balloon 18. During operation, coolant may flow from a coolant supply reservoir 62 through a fluid delivery conduit 42 within the elongate body 20 to the distal portion 26, where the coolant may then enter the interior chamber 60 of the balloon 18, such as through the one or more fluid delivery elements 58, where the coolant may expand to cool the balloon 18. Expanded coolant may then pass from the interior chamber 60 of the balloon 18 to a coolant recovery reservoir 64 and/or scavenging system through the fluid return conduit. Further, as is discussed in greater detail below, the size of the balloon 18 when fully inflated may be chosen by the user based on various factors such as the patient's anatomy and pulmonary vein ostium diameter, and may also be independent of the flow rate of and fluid pressure generated by delivery of the coolant to the balloon 18.

The treatment device 12 further includes a handle 66 coupled to the elongate body proximal portion 24. The handle 66 includes one or more steering or deflection components for manipulating the elongate body 20, the one or more treatment elements 16, and/or additional components of the treatment device 12. In one embodiment, the handle 66 includes an actuator element or push button 68 that is in direct mechanical communication with the proximal portion of the shaft 48. In one embodiment, the push button 68 is a slide mechanism that is longitudinal movable within or relative to the handle 66. In this embodiment, movement or actuation (for example, longitudinal movement) of the push button 68 exerts a direct force on the shaft 48 and causes the shaft 48 to likewise slide, or move longitudinally, within the elongate body 20. As the distal neck 56 of the balloon 18 is coupled to the distal portion 50 of the shaft 48, this longitudinal movement of the shaft 48 caused by engagement of the push button 68 will cause a change in the shape and/or size of the balloon 18, as is discussed in greater detail below. Further, the handle 66 is fixedly coupled to the elongate body proximal portion 24 and the push button 68 is mechanically coupled to the shaft 48; however, in one embodiment, the push button 68 and shaft 48 are freely movable with respect to the handle 66 and elongate body 20 (even though the push button 68 may be at least partially disposed within the handle), thereby allowing the push button 68 and shaft 48 to move based on the balloon pressure without actuation or control by the user. That is, when the push button 68 is not engaged by the user, both the push button 68 and the shaft 48 are, in one embodiment, freely longitudinally movable relative to the handle 66 and the elongate body 20, based on the force exerted on the shaft distal portion 50 by the inflation pressure of the balloon 18. The handle 66 also includes connectors that are matable directly or indirectly to the control unit 14 to establish communication between the one or more components of the treatment device 12 with one or more components of the control unit 14, as described herein.

Figure 21:
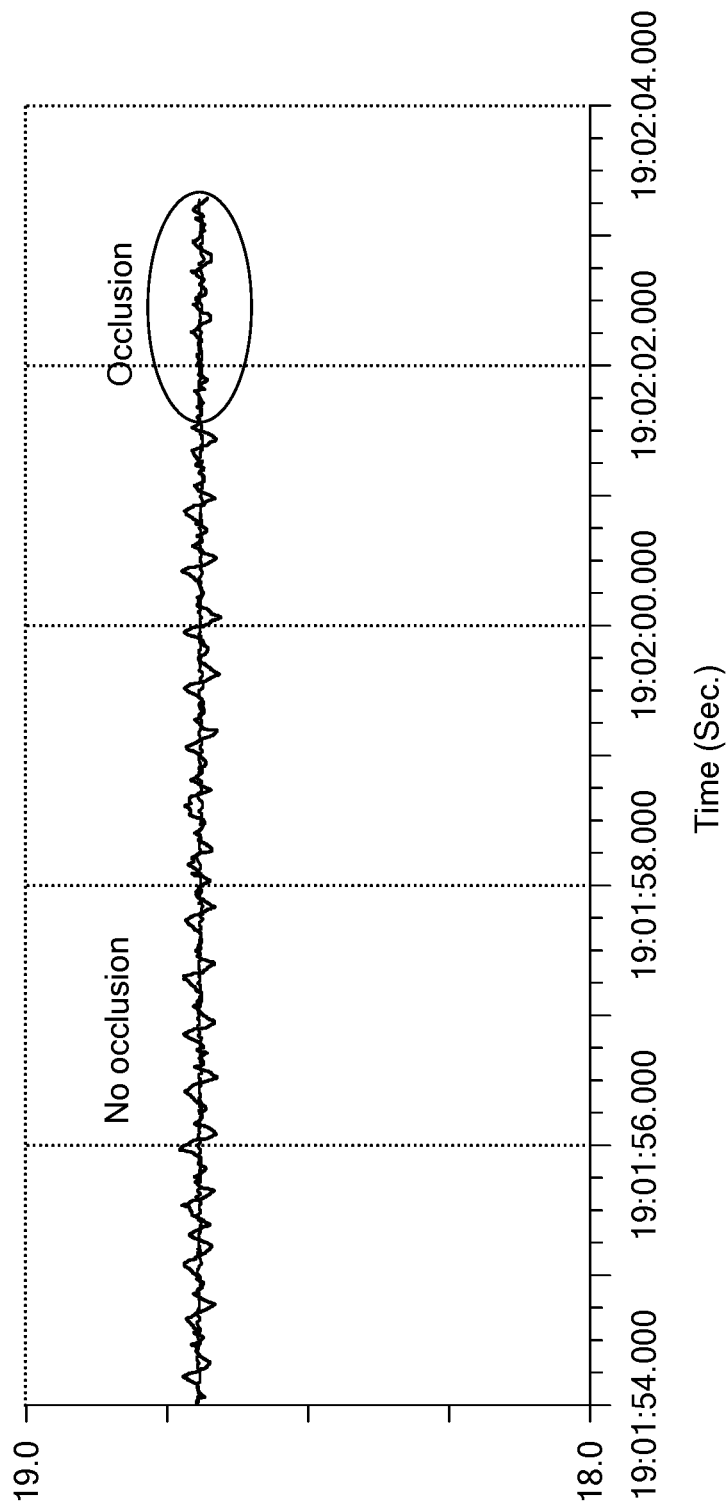
FIG. 21 shows a graph of pressure over time for the assessment of vessel occlusion.

In one embodiment, the treatment device 12 and/or the control unit 14 includes one or more sensors. In one non-limiting example, the treatment device 12 includes one or more pressure sensors 70 on and/or within the balloon 18. These pressure sensors 70 are configured to record pressure waves from or through the balloon 18, such as pressure waves generated by the beating of the patient's heart. As is shown in FIG. 21, the magnitude or value of the pressure waves recorded by the sensor(s) 70 may be used to determine whether the balloon 18 is completely occluding a vessel, such as a pulmonary vein ostium. As the balloon 18 is used at low pressures (for example, <6 psig), it is possible to accurately monitor the patient's heartbeat with the pressure sensor(s) 70. As the vessel is occluded, the pressure signal (that is, the pressure waves generated by the heartbeat) becomes less pronounced, indirectly proportional to the quality of occlusion of the vessel. In one non-limiting example, a relatively flat signal may indicate adequate occlusion.

Figure 4:
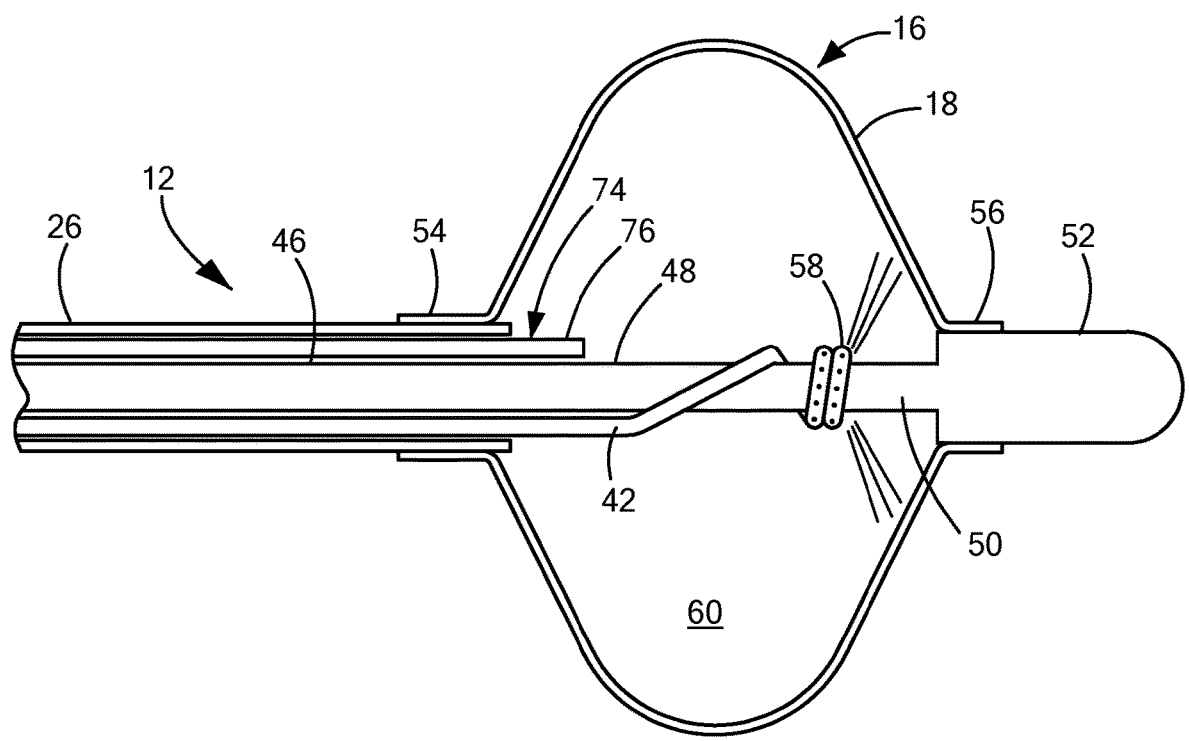
FIG. 4 shows a cross-sectional view of an exemplary medical device, such as the medical device shown in FIG. 1.

Additionally or alternatively, one or more sensors may be used to evaluate inflation and/or configuration of the balloon 18. For example, in one embodiment, the control unit 14 includes a pressure sensor 72 that is in fluid communication with a Pitot tube 74 in the treatment device 12. The Pitot tube 74 may be composed of polyimide or similar material(s) and may have an outer diameter of approximately 0.030 in. In one embodiment, the Pitot tube 74 includes a distal end 76 that is at least partially located within the interior chamber 60 of the balloon 18 and a proximal end 77, opposite the distal end 76, that contains, is coupled to, or otherwise in communication with the pressure sensor 72. The Pitot tube distal end 76 includes an opening that is exposed to fluid circulating within the interior chamber 60. The Pitot tube 74 is used to measure the pressure at the stagnation point ($P_{stag}$), which is the pressure within the interior chamber 60 proximate the opening at the distal end 76 (for example, as shown in FIG. 4), based on the dynamic pressure ($P_{dynamic}$) and static pressure ($P_{static}$) of the fluid within the interior chamber 60:

$$P_{stag} = P_{static} + P_{dynamic} \quad (1)$$

where $$P_{dynamic} = (\rho * v^2)/2 \quad (2)$$

As is discussed in greater detail below, the velocity of fluid (for example, coolant) circulating within the balloon 18 is relatively low, especially near the opening at the Pitot tube distal end 76. Therefore:

$$P_{dynamic} = 0 \quad (3)$$

and $$P_{stag} = P_{static} \quad (4)$$

Thus, the fluid pressure measured by the Pitot tube 74 at the stagnation point ($P_{stag}$) can be used to directly determine the static pressure ($P_{static}$) of the fluid within the interior chamber 60 (that is, the balloon pressure). However, it will be understood that a Pitot-static tube may be used instead of a Pitot tube. Additionally or alternatively, other components may be used to determine pressure, such as a piezo-resistive MEMS, fiber optic system based on the Fabry-Perot principal, capacitive resistors, thermistors, and the like. Determining the pressure within the interior chamber 60 allows the user and/or the control unit 14 to set the balloon 18 diameter based on the determined pressure, monitor the balloon 18 pressure to prevent over pressurization, and/or monitor a push force on the treatment device 12 or portion thereof when in use.

In one embodiment, the coolant supply reservoir 62, coolant recovery reservoir 64, and/or one or more alternative energy sources to supply the selected modality of treatment to the treatment element(s) 16 (such as, for example, a radiofrequency generator, ultrasound generator, light sources, or the like) as well as various control mechanisms for the medical system 10 are housed in the control unit 14. For example, if a fluid other than a coolant is used to inflate the balloon 18, the control unit 14 may also include an inflation fluid reservoir. The control unit 14 also includes one or more computers 78 having one or more displays 80 and processing circuitry 82 and/or software modules. The processing circuitry 82 may be programmed or programmable to execute the automated operation and performance of the features, sequences, or procedures described herein. As a non-limiting example, the processing circuitry 82 includes a memory and a processor, the memory in communication with the processor and having instructions that, when executed by the processor, configure the processor to perform one or more system functions. For example, the processing circuitry 82 may be configured to receive electrical signals from the pressure sensor(s) 70, 72 to evaluate vessel occlusion by the balloon 18 and/or to determine fluid flow rates and/or balloon pressure. It will be understood that one or more system components may be physically located outside of the control unit 14; however, any system components that are not part of the treatment device 12 may be referred to herein as being located within the control unit 14 for simplicity. In one embodiment, the control unit 14 (for example, the processing circuitry 82) is configured to compare one or more determined pressure values ($P_{stag}$ and/or $P_{static}$, for example) to a threshold pressure to determine if the balloon 18 is being maintained at a pressure of between 0.2 psig and 3.0 psig. Additionally or alternatively, the control unit 14 is configured to compare determined pressure values ($P_{stag}$ and/or $P_{static}$, for example) to each other during the procedure. For example, the control unit 14 may be configured to compare a determined pressure value recorded during the inflation phase to a determined pressure value recorded during the ablation phase.

Figure 5:
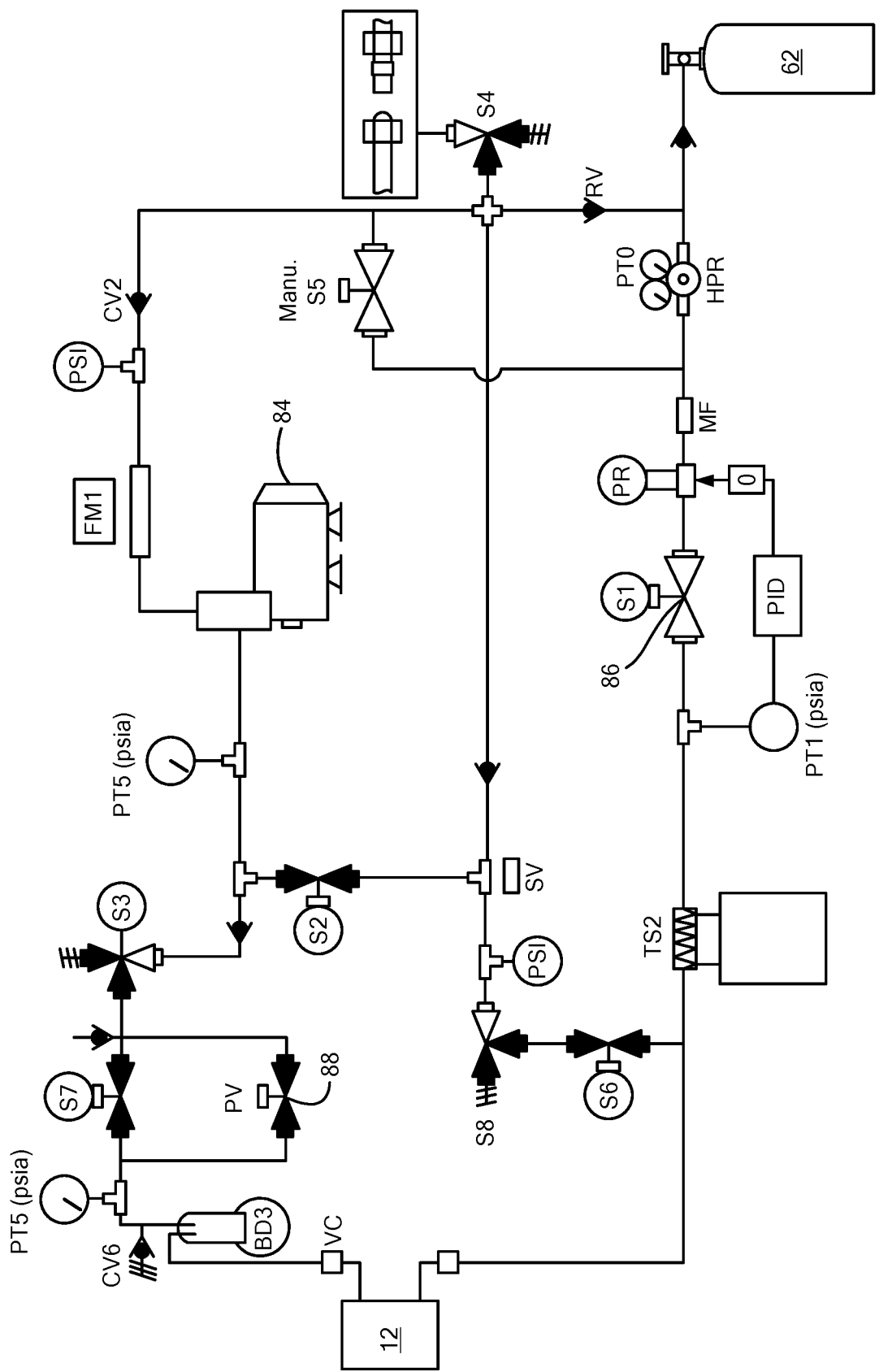
FIG. 5 shows a schematic view of the exemplary medical system of FIG. 1.
Figure 6:
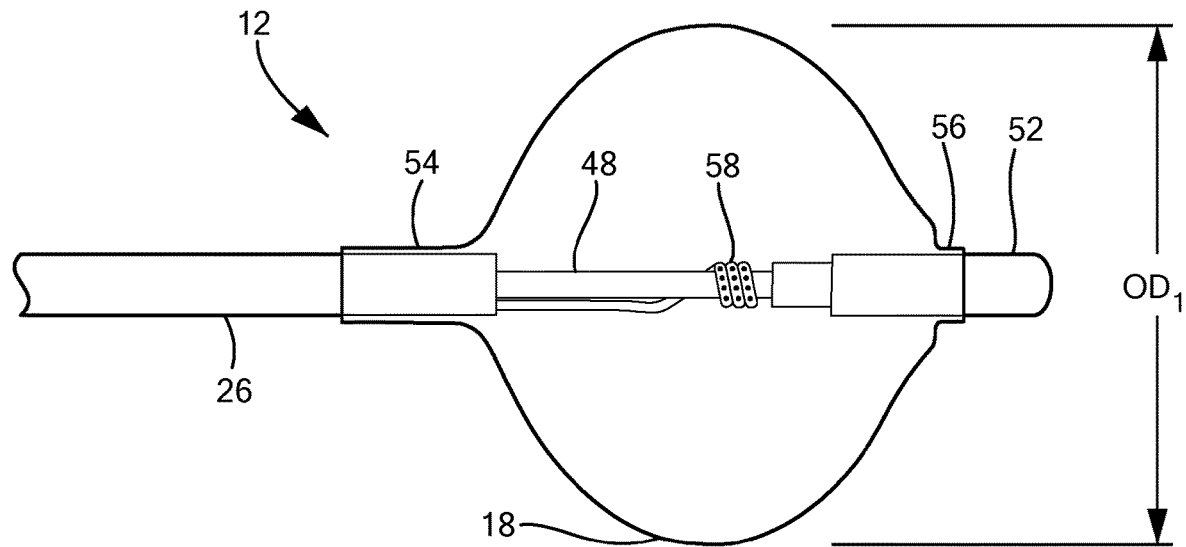
FIG. 6 shows a highly conformable balloon in an expanded first configuration with a first outer diameter.
Figure 7:
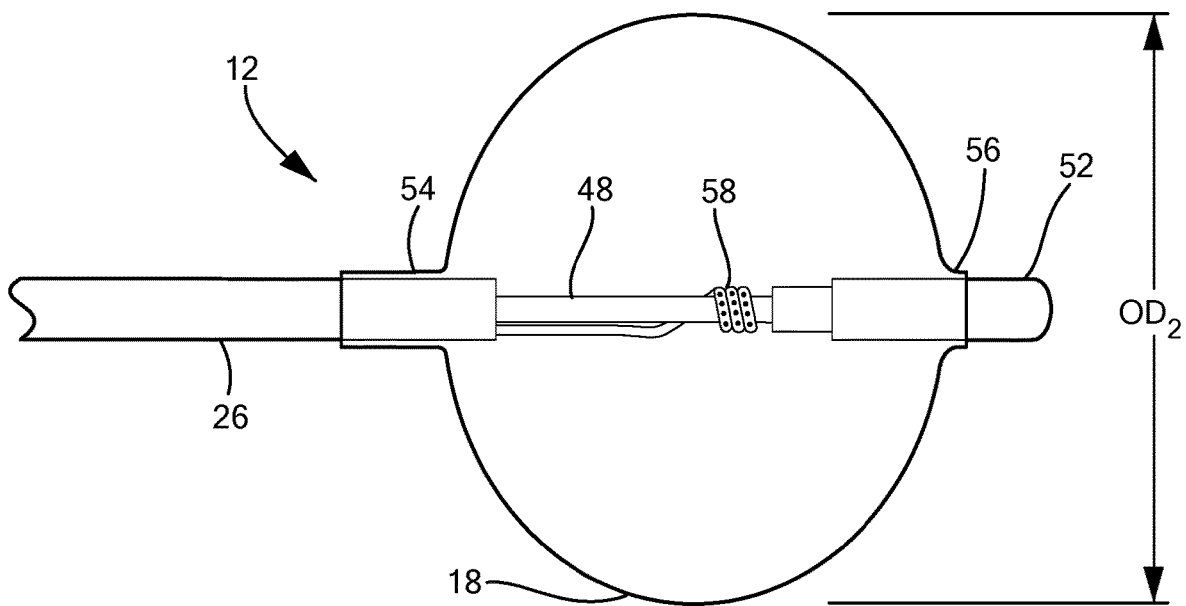
FIG. 7 shows the highly conformable balloon in the expanded first configuration with a second outer diameter.

Referring now to FIGS. 5-20, inflation of the balloon 18 will now be discussed in greater detail. In one embodiment, the balloon 18 is a highly conformable balloon that may be inflated to a variety of outer diameters, while maintaining a high degree of flexibility or conformity to the contour of an object (such as a tissue surface) with which the balloon 18 is in contact. For example, when the balloon 18 is inflated to have an at least substantially round first configuration, the balloon 18 may be inflated to a first outer diameter $OD_1$, such as approximately 23 mm (±2 mm) (as shown in FIG. 6). If desired, the balloon 18 may be further inflated to a larger second outer diameter $OD_2$, such as approximately 36 mm (±2 mm) (as shown in FIG. 7). Of course, the balloon 18 may be inflated to any outer diameter between the first and second outer diameters, depending on the procedure, patient's anatomy, user's preference, or the like. Regardless of the outer diameter of the balloon 18, however, the balloon 18 remains highly compliant. The fluid, such as coolant, used to inflate the balloon 18 may be delivered to the interior chamber 60 at a pressure of between 0.2 psig and 3.0 psig. The medical system 10 may further include one or more flow control valves in fluid flow pathways of the medical system 10 and a vacuum pump or vacuum source 84 to remove fluid from the balloon interior chamber 60. For example, the medical system 10 (for example, the control unit 14) may include a flow control valve 86 in communication with the fluid delivery conduit 42 and a pressure control valve 88 in communication with the fluid return conduit 46 (for example, as shown in FIG. 5).

In one embodiment, the push button 68 and shaft 48 is freely movable with respect to the handle 66 and the elongate body 20. As the balloon 18 inflates, the shaft 48 is free to move and takes its position based on the differential pressure between both sides of the balloon 18. As the outer diameter of the balloon 18 increases with pressure, the balloon 18 length also increases, as movement (in this case, movement in a proximal-to-distal direction) of the shaft 48 is not constrained, as in currently known devices.

Figure 8:
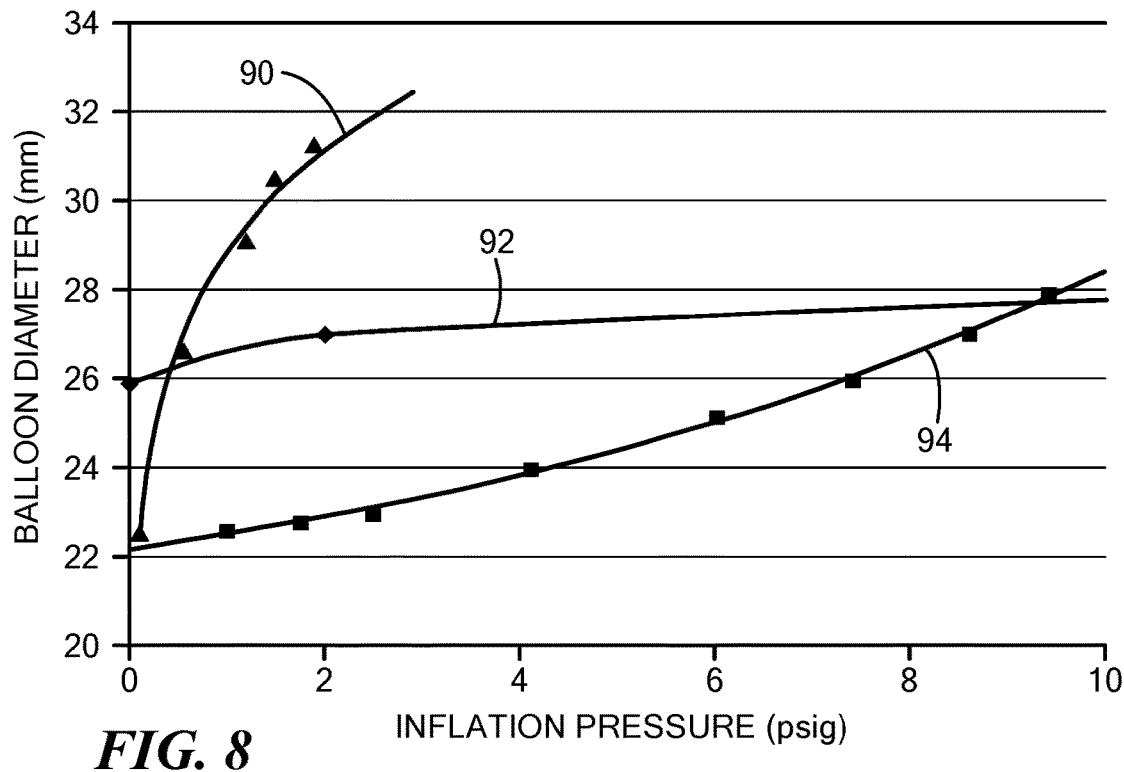
FIG. 8 shows a chart of balloon diameter versus inflation pressure.
Figure 9:
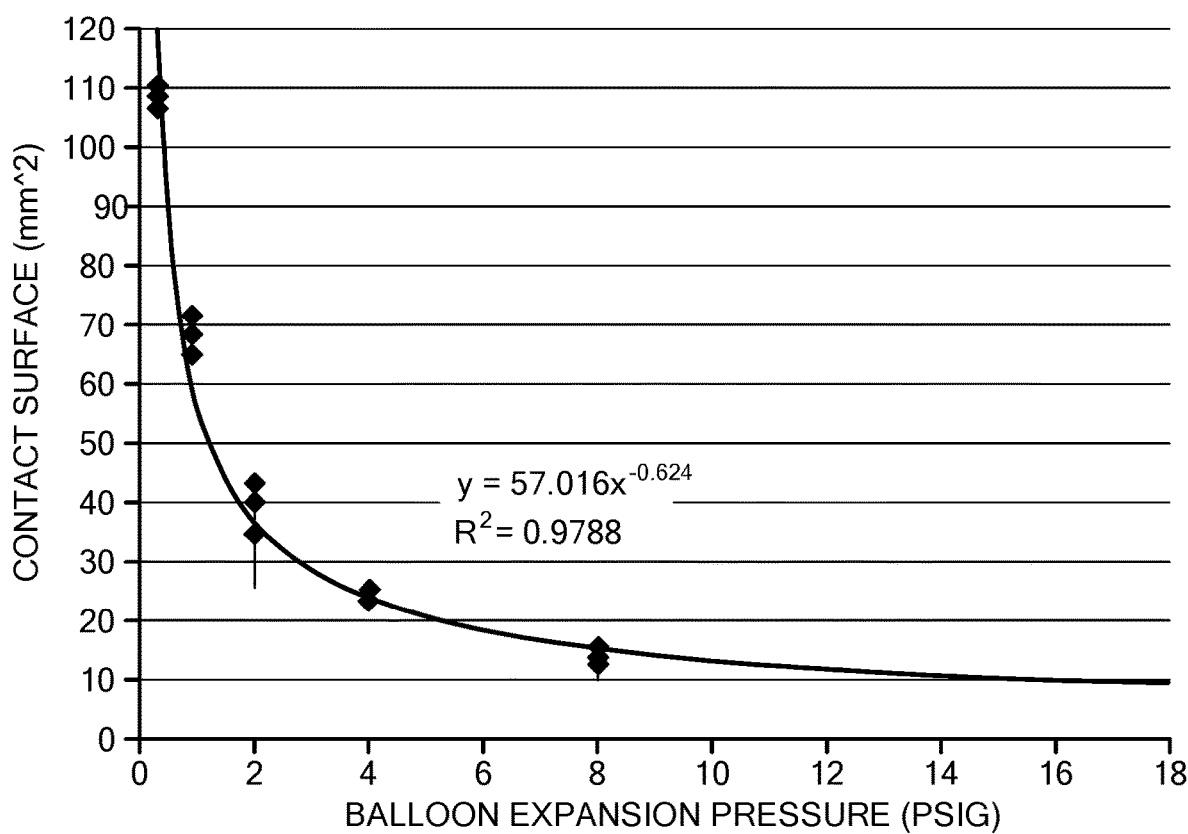
FIG. 9 shows a chart of tissue contact surface area on the balloon versus inflation pressure.

A comparison of balloon diameter and inflation pressure between a balloon 18 of the present disclosure and two currently known balloon devices is shown in FIG. 8. The curve 90 for the balloon 18 of the present disclosure shows that inflation of the balloon even at low inflation pressures (for example, up to 3.0 psig) results in a rapid increase in the balloon outer diameter. In contrast, the curves 92, 94 for currently known balloon devices show a much slower increase in balloon outer diameter with increase in inflation pressure. FIG. 9 shows a chart of tissue contact surface area on the balloon 18 versus inflation pressure. In some embodiments, a lower inflation pressure results in a larger tissue contact surface area.

Figure 10:
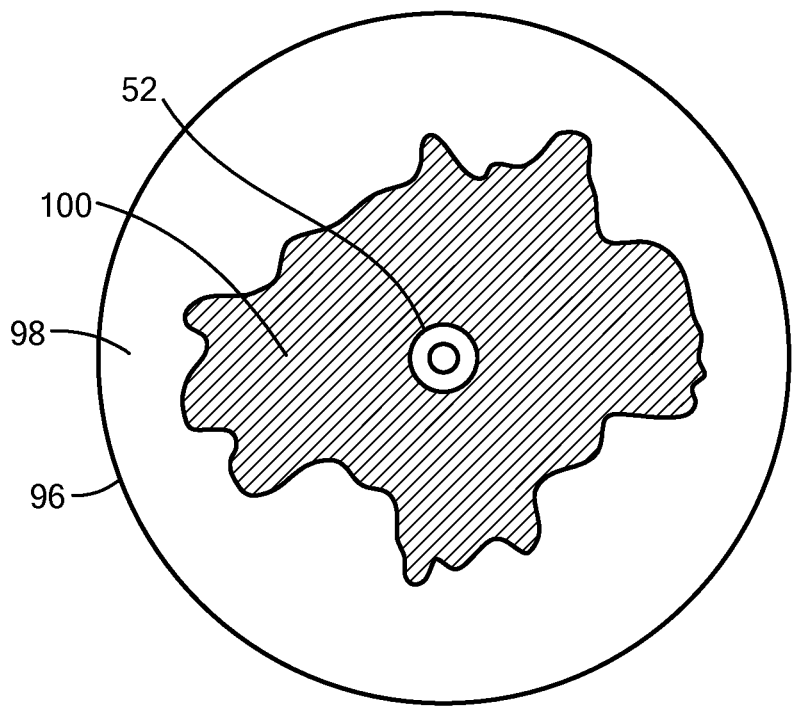
FIG. 10 shows a front view of a currently known balloon and an exemplary tissue contact area on the distal face of the currently known balloon.
Figure 11:
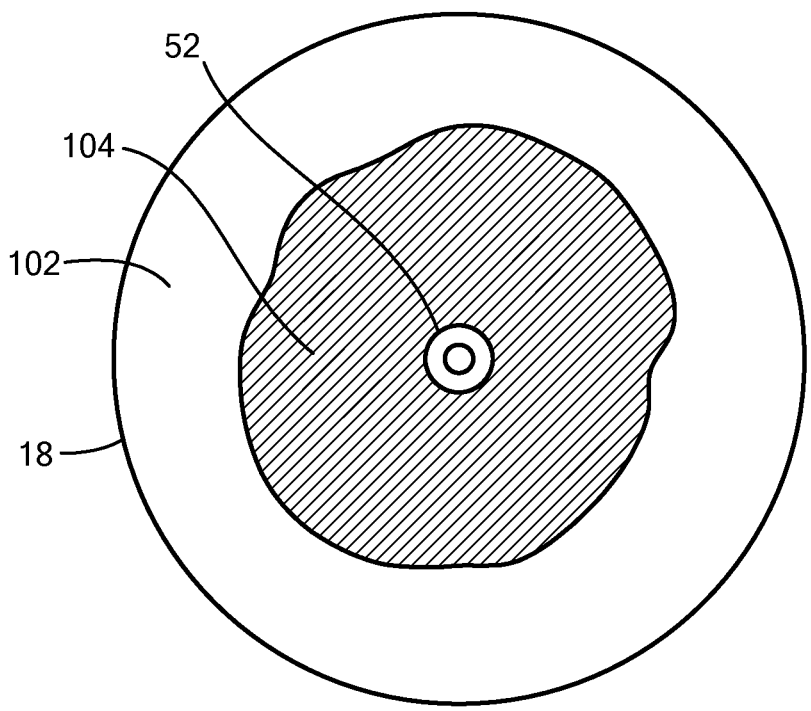
FIG. 11 shows a front view of a medical device having a highly conformable balloon disclosed herein in the expanded first configuration and an exemplary tissue contact area on the distal face of the highly conformable balloon.

Referring now to FIGS. 10-27, use of the treatment device 12 is discussed in greater detail. FIGS. 10 and 11 show use of the distal face of a currently known balloon 96 and the balloon 18 of the present disclosure, respectively, to ablate an area of targeted tissue. As discussed above, the balloon 18 of the present disclosure, even when inflated, is highly conformable (that is, the balloon 18 is "soft"). Consequently, pushing the balloon 18 against an area of targeted tissue, even when pushed gently, causes the balloon 18 to deform such that a larger surface area of the balloon 18 is in contact with the area of targeted tissue. FIG. 10 shows a front view of a currently known balloon 96 (that is, the distal face 98), with an exemplary tissue contact area 100 illustrated. FIG. 11 shows a front view of the balloon 18 (that is, the distal face 102) of the present disclosure, with an exemplary tissue contact area 104 illustrated. The comparison of FIGS. 10 and 11 shows that the high compliance or softness of the balloon 18 results in a larger, more uniform tissue contact surface, which, in turn, results in more efficient lesion formation. When in the balloon 18 is in the at least substantially round first configuration, the treatment device 12 may be used for a variety of procedures, such as pulmonary vein isolation. Although the treatment device 12 is shown in the figures as having a shaft distal tip 52 that protrudes beyond the distal face 102 of the balloon 18, it will be understood that the treatment device 12 may alternatively have an atraumatic, substantially continuous distal face 102, without the protruding shaft distal tip 52.

Figure 12:
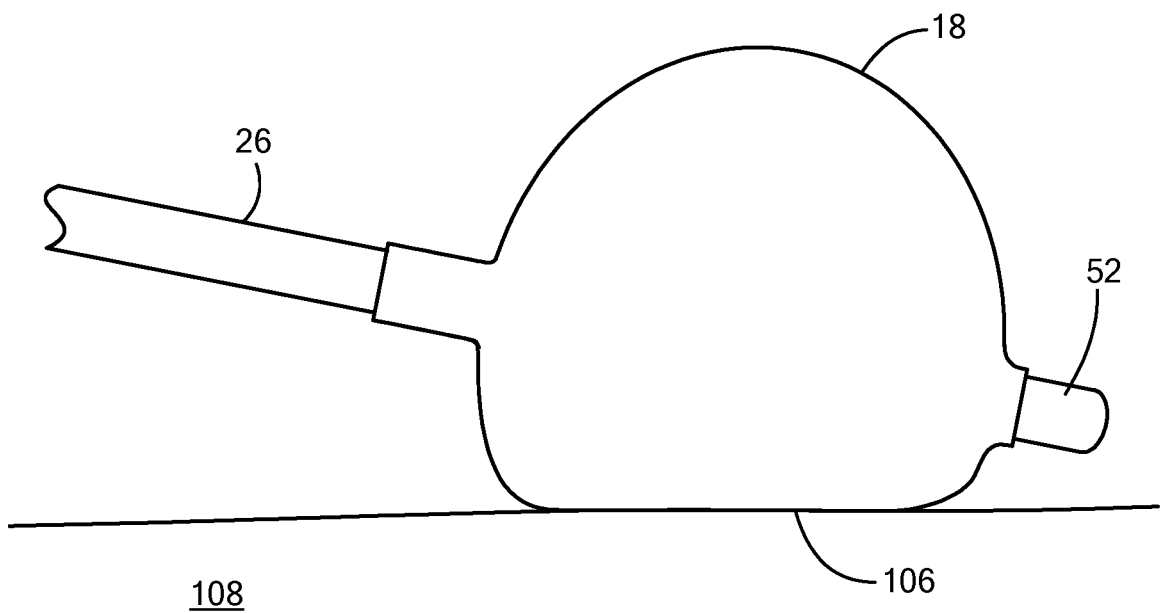
FIG. 12 shows a side view of an exemplary highly conformable balloon in the expanded first configuration and in contact with an area of targeted tissue.
Figure 13:
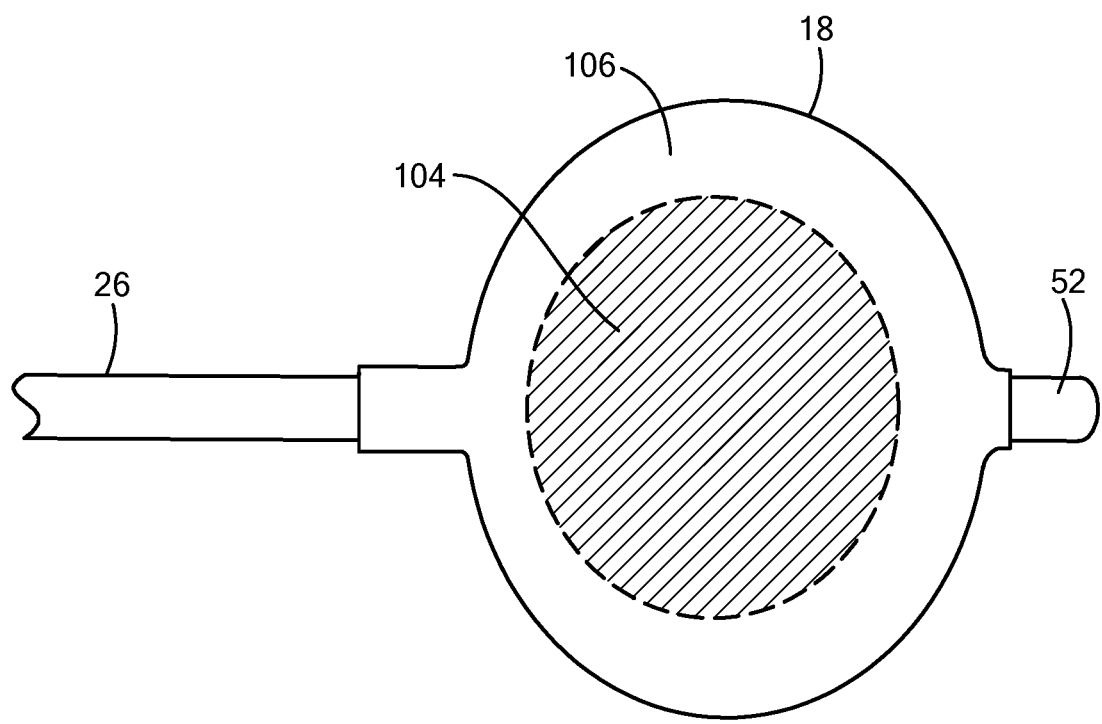
FIG. 13 shows a contact surface of the highly conformable balloon of FIG. 11 when the highly conformable balloon is in the expanded first configuration and in contact with the area of targeted tissue.
Figure 14:
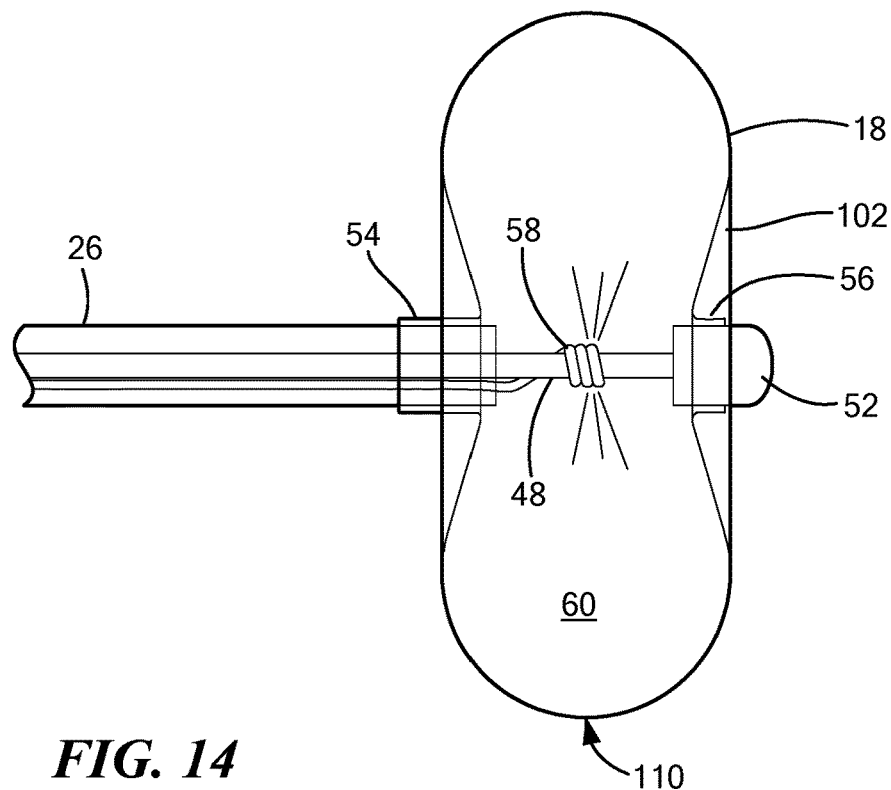
FIG. 14 shows a side view of the exemplary highly conformable balloon in an expanded second configuration.
Figure 15:
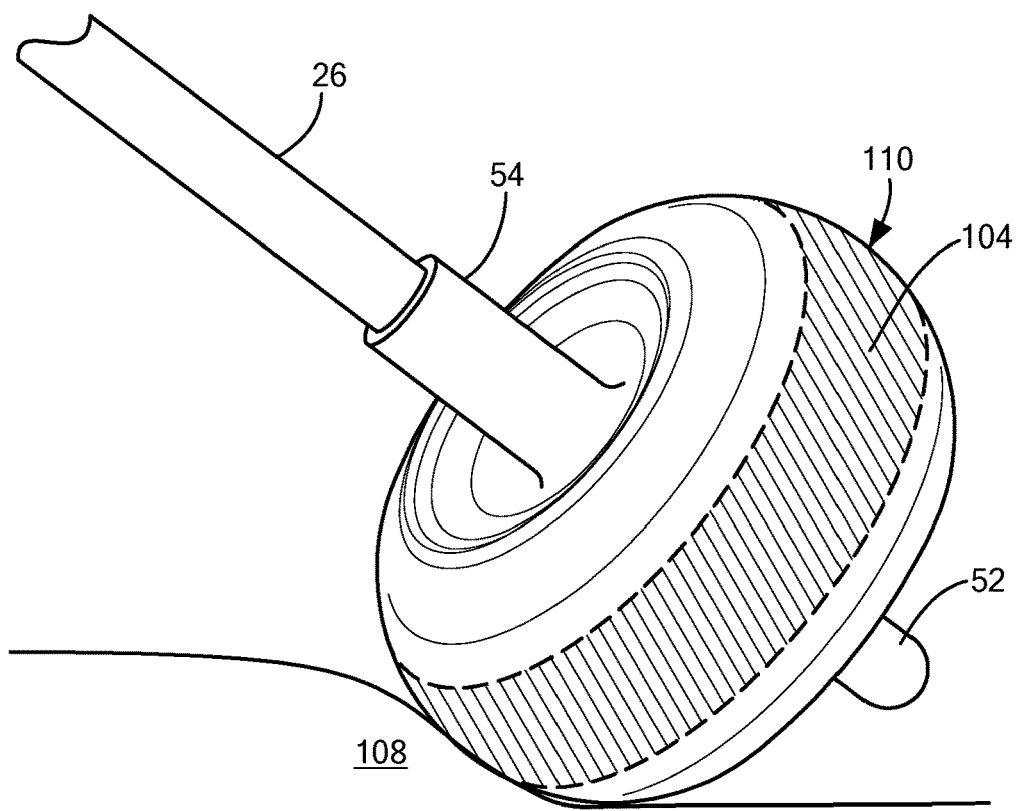
FIGS. 15 and 16 show rear and front perspective views, respectively, of the highly conformable balloon of FIG. 13 and a contact surface of the highly conformable balloon when the highly conformable balloon is in the expanded second configuration and in contact with an area of targeted tissue.
Figure 16:
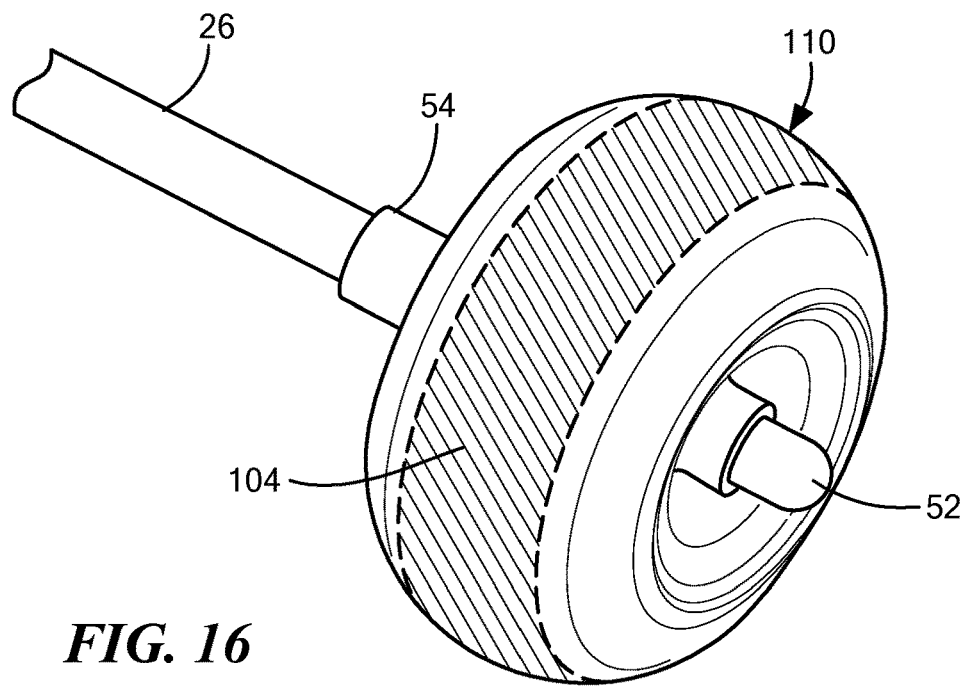

This same principal is also applicable when a lateral surface of the balloon 18 is used to ablate an area of targeted tissue, which is shown in FIGS. 12 and 13. For example, FIG. 12 shows a side view of an inflated highly conformable balloon 18 when the lateral surface 106 of the balloon 18 is in contact with an area of targeted tissue 108, and illustrates that the balloon 18, when pushed against the area of targeted tissue 108, flattens to create a larger, more uniform tissue contact area 104. The lateral surface 106 of the balloon 18 is shown in FIG. 13, with an exemplary tissue contact area 104 on the lateral surface 106 when the balloon 18 is in contact with an area of targeted tissue illustrated.

FIGS. 11-13 show use of the balloon 18 when the balloon is in the at least substantially round first configuration. For example, the balloon 18 may be inflated to be spherical, ovate, obovate, ellipsoid, or any other shape in which the proximal 54 and distal 56 necks of the balloon 18 are outside of the interior chamber 60. In contrast, FIGS. 14-17 show use of the lateral surface 106 of the balloon 18 to ablate an area of targeted tissue 108 when the balloon 18 is in an at least substantially toroidal second configuration. In this configuration, the balloon 18 may be positioned against the area of targeted tissue 108 such that the tissue contact area 104 is located around the equator or outer circumference 110 of the balloon 18. When the balloon 18 is in the at least substantially toroidal second configuration, the treatment device 12 may be used to, for example, ablate rotors (rotating areas of aberrant electrical currents) and/or to create spot lesions in the area of targeted tissue.

Figure 17:
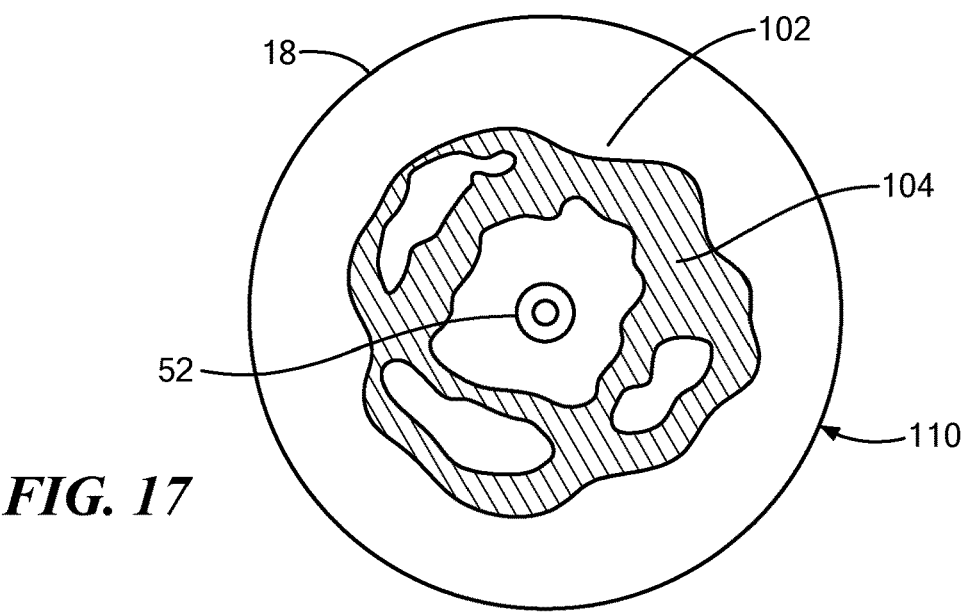
FIG. 17 shows a front view of the exemplary highly conformable balloon in the expanded second configuration and an exemplary tissue contact area on the distal face of the highly conformable balloon when the distal face of the highly conformable balloon is in contact with an area of targeted tissue.

In one embodiment, the balloon 18 is transitioned from the at least substantially round first configuration to the at least substantially toroidal second configuration by engagement with or actuation of the push button 68, which moves the shaft 48 within the elongate body 20 in a distal-to-proximal direction, resulting in inversion of the proximal 54 and distal 56 necks of the balloon 18 into the interior chamber 60 (as shown in FIGS. 14-17). In an embodiment in which the fluid delivery element(s) 58 are coupled to, located within, or otherwise associated with the shaft 48, retraction of the shaft 48 also brings the fluid delivery element(s) 58 toward the equator 110 of the balloon 18 to focus the cooling effect of circulation of coolant within the interior chamber 60 toward the equator 110, thus forming a lateral surface for efficient tissue ablation. In contrast, the distal face 98 of the balloon 18 may be less suited for ablating the area of targeted tissue, as the tissue contact area 104 on the distal face 102 of FIG. 17 shows.

Figure 18:
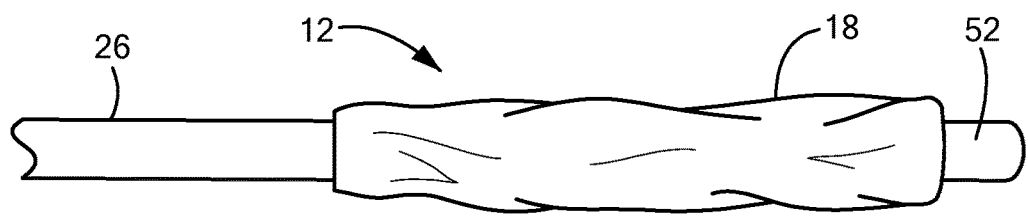
FIG. 18 shows a side view of the exemplary highly conformable balloon in a delivery configuration.
Figure 19:
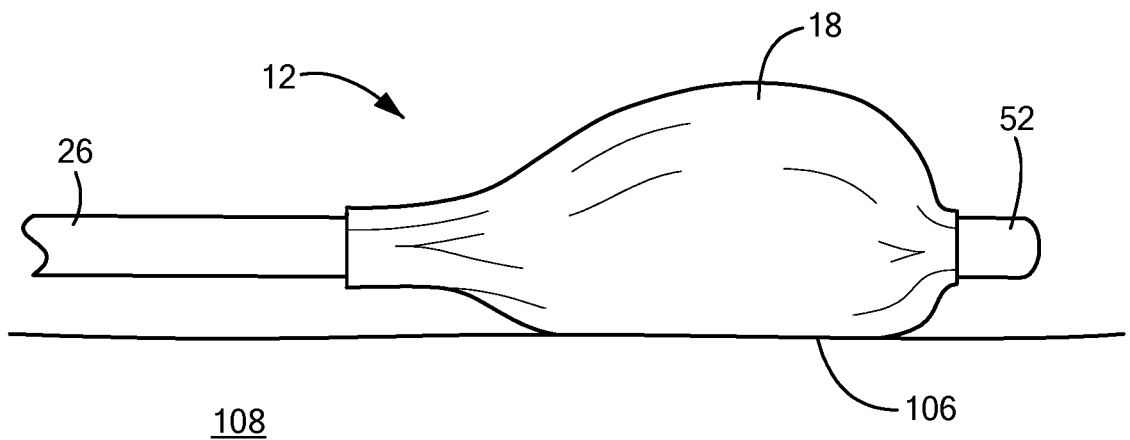
FIG. 19 shows a side view of the exemplary highly conformable balloon in an expanded third configuration and in contact with an area of targeted tissue.
Figure 20:
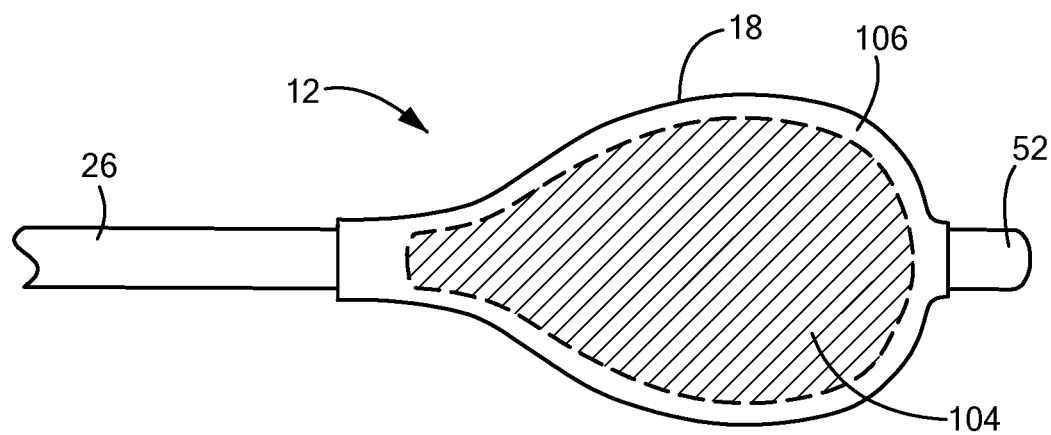
FIG. 20 shows an exemplary tissue contact area of the highly conformable balloon of FIG. 19 when the highly conformable balloon is in the expanded third configuration and in contact with the targeted area of tissue.

FIGS. 18-20 show use of the lateral surface 106 of the balloon 18 to ablate an area of targeted tissue 108 when the balloon 18 is in an at elongated third configuration. In one embodiment, the balloon 18 is initially in a delivery configuration in which the balloon 18 is uninflated (as shown in FIG. 18). Once proximate the area of targeted tissue, the balloon 18 is inflated only partially or not inflated at all (that is, inflation pressure is below the arterial pressure) and the shaft 48 is extended within the elongate body 20 in a proximal-to-distal direction (for example, by actuation of the push button 68 by the user) from the initial position to elongate the balloon 18 and create a relatively large tissue contact area 104 when the lateral surface 106 is in contact with the area of targeted tissue 108 (for example, as shown in FIGS. 19 and 20). In this configuration, the balloon 18 may be used to create linear, at least substantially linear, or elongated lesions (for example, when creating a mitral isthmus isolation line). As the circulation (flow rate) of coolant within the interior chamber 60 is controllable independently of the inflation pressure (flow volume through the delivery and return conduits and/or strength of the vacuum source), the balloon 18 may be used to ablate the area of targeted tissue even when in a most deflated or partially inflated state.

Figure 23:
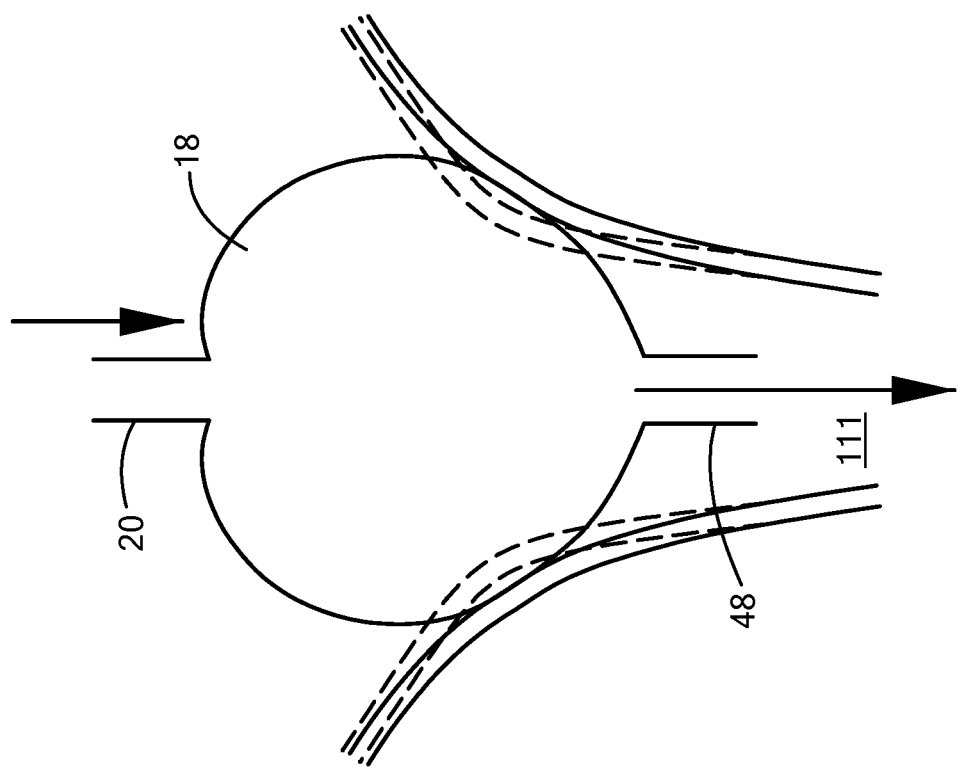
FIGS. 22-24 show various means of occluding a vessel with a highly compliant balloon.
Figure 22:
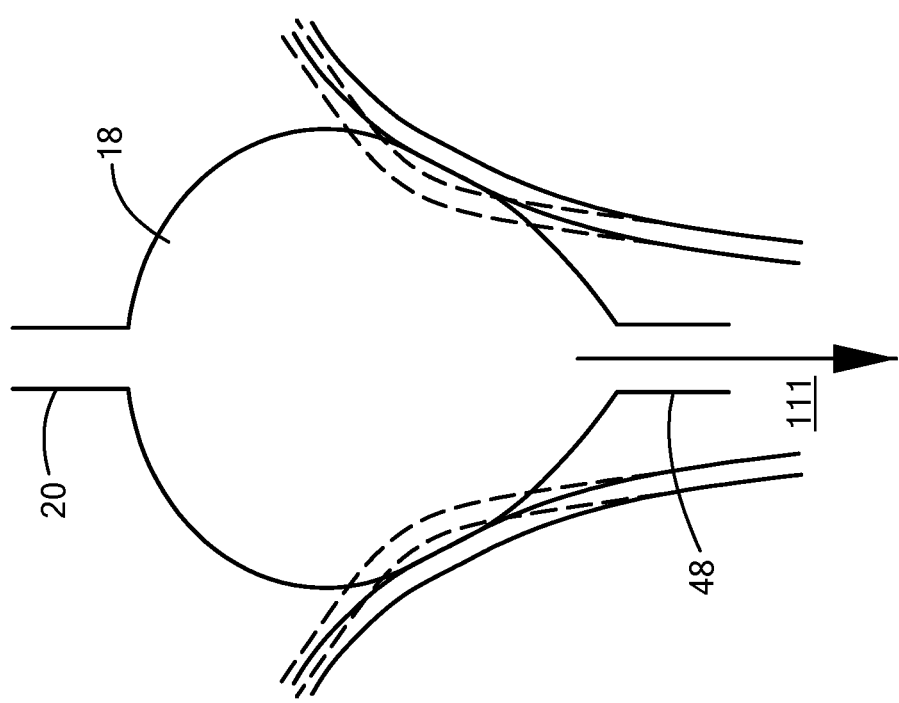
Figure 25:
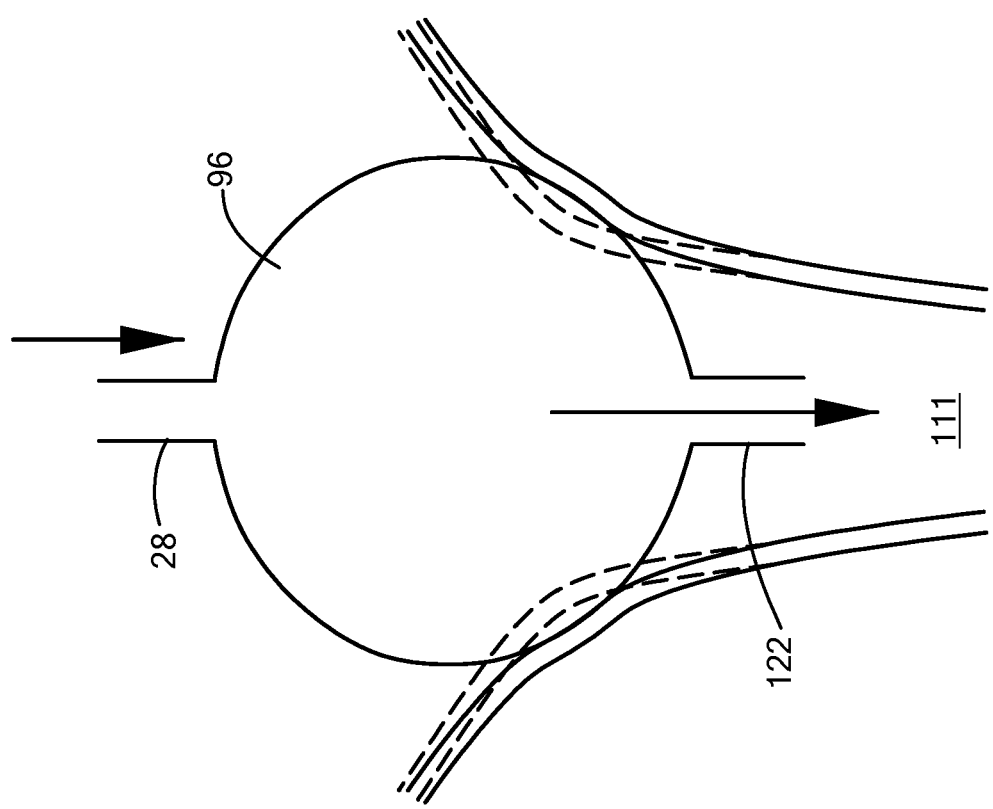
FIG. 25 shows a means of occluding a vessel with a currently known balloon.
Figure 24:
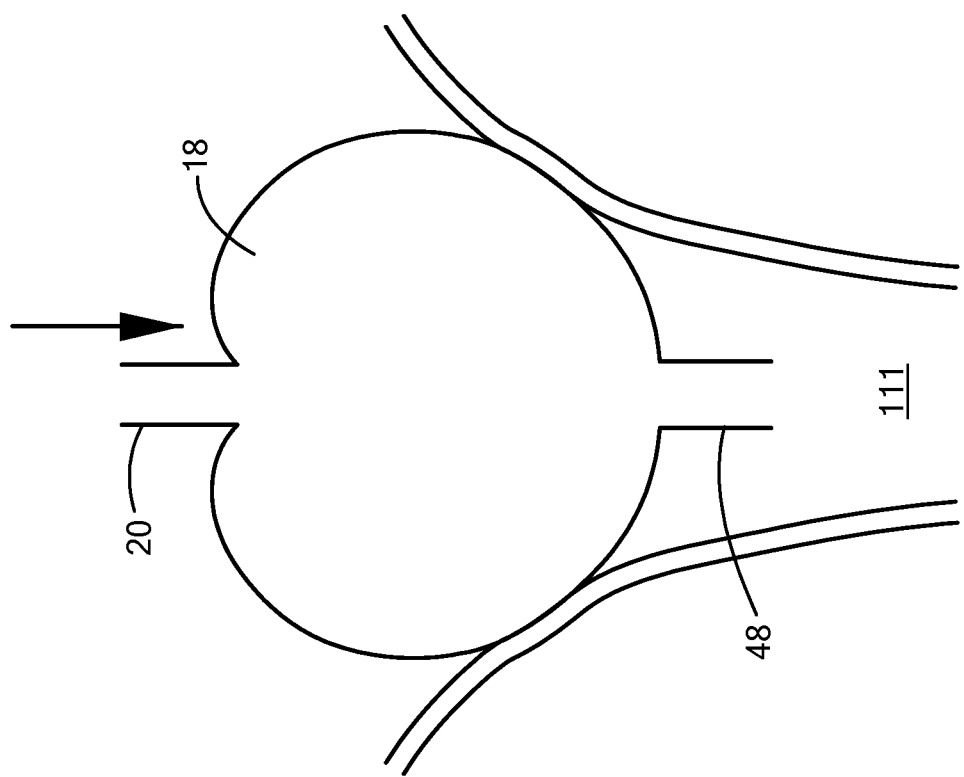
Figure 26:
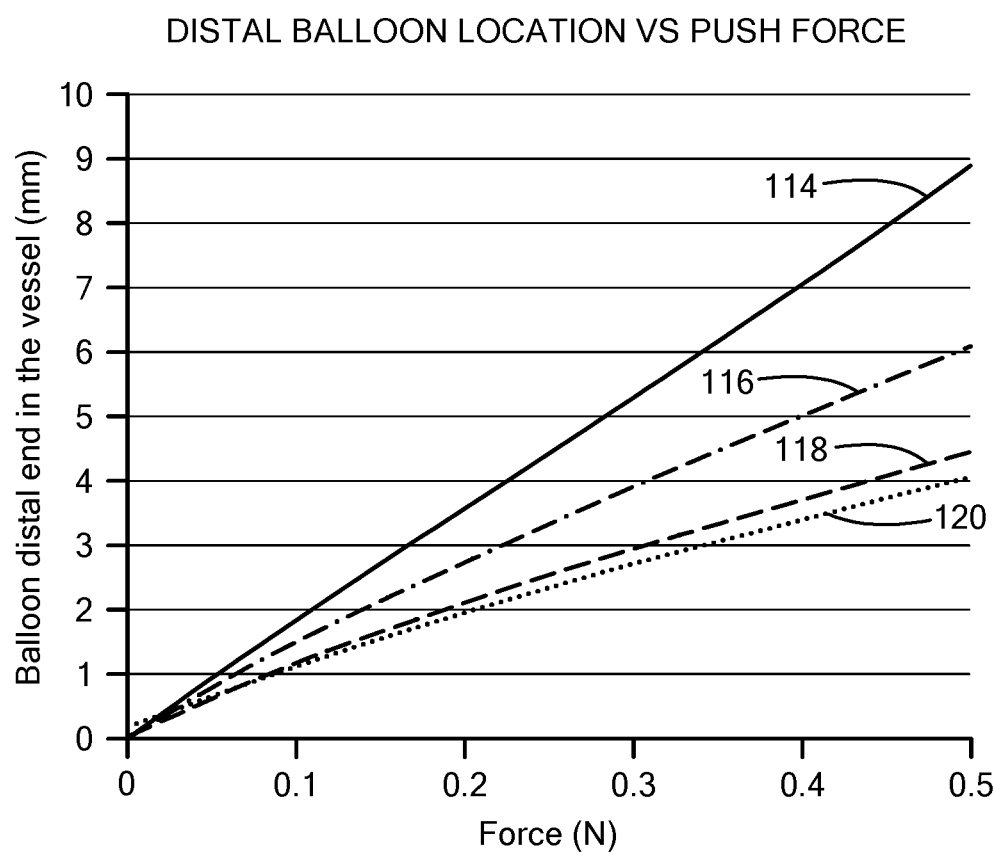
FIG. 26 shows a chart comparing the depth into the vessel the balloon distal end may travel as a function of force.

The treatment device 12 with the highly compliant balloon 18 disclosed herein may also be used to safely occlude a vessel, such as when performing pulmonary vein isolation, without causing the distal end of the treatment device 12 (for example, the shaft distal tip 52 and distal portion of the balloon 18) from traveling too far into the vessel. The deeper into the vessel the balloon travels, the higher the risk of tamponade, aneurysm, and/or phrenic nerve injury. FIGS. 22-24 show a treatment device 12 having a highly compliant balloon 18 used to occlude a vessel 111 and FIG. 25 shows a treatment device 112 having a balloon 96 used to occlude a vessel 111. FIG. 26 shows a chart comparing the depth into the vessel 111 the balloon 18, 96 distal end may travel as a function of force, with lines 114, 116, 118, and 120 representing the scenarios of FIGS. 22-25, respectively. Current perception in the art is that a compliant balloon inflated at a low pressure would tend to travel too far into the vessel during occlusion. However, the treatment device 12 of the present disclosure does not present this problem. As the shaft 48 is freely movable when the push button 68 is not engaged by the user, the axial force provided by the user at the handle 66 during occlusion is not transferred, or is transferred by only a small degree, to the shaft 48 (and shaft distal tip 52). Instead, axial force provided by the user at the handle 66 will be transmitted through the elongate body 20 and, consequently, to the rear of the balloon 18. This causes the balloon to increase in diameter and, as a result, prevents the balloon 18 from traveling into the vessel 111 to an unacceptable or unsafe depth.

This phenomenon may be analogized to moving a rope through a hole: it may be very difficult to push the rope through the hole, but very easy to pull the rope through the hole. FIG. 22 shows a first method of occluding a vessel 111 with a highly conformable balloon 18 in which the axial force provided by the user is transmitted through the shaft 48 only (similar to pulling the "rope" through the "hole"), as depicted by the arrow. For example, the balloon 18 is inflated to an outer diameter of 28 mm at 1.0 psig. FIG. 23 shows a second method of occluding a vessel 111 with a highly conformable balloon 18 in which the axial force provided by the user is transmitted through the shaft 48 (similar to pulling the "rope" through the "hole") and is transmitted through the elongate body 20 (similar to pushing the "rope" through the "hole"), as depicted by the arrows. For example, the balloon 18 is inflated to an outer diameter of 28 mm at 1.0 psig. FIG. 24 shows a third method of occluding a vessel 111 with a highly conformable balloon 18 in which the axial force provided by the user is transmitted through the elongate body 20 only (similar to pushing the "rope" through the "hole"), as depicted by the arrow. For example, the balloon 18 is inflated to an outer diameter of 28 mm at 1.0 psig. Finally, FIG. 25 shows a method of occluding a vessel 111 with a currently known (that is, not highly conformable) balloon 96 in which the axial force provided by the user is transmitted through the elongate body 28 and/or the shaft 122. As the balloon 96 is more rigidly inflated, transmitting axial force through the elongate body 28 versus the shaft 122 may have the same, or approximately the same, effect on the balloon 96. Consequently, arrows are shown in FIG. 25 to depict axial force transmitted to the elongate body 28 and/or the shaft 122. For example, the balloon 96 is inflated to an outer diameter of 28 mm at a pressure of 18 psig.

As can be seen by FIGS. 22-25 and the accompanying chart in FIG. 26, transferring the axial force generated by the user on the handle 66 to the shaft 48 effectively "pulls" the highly conformable balloon 18 into the vessel 111 by proximal-to-distal movement of the shaft 48 (which elongates and reduces the outer diameter of the balloon 18, making it easier for the balloon 18 to travel into the vessel). However, transferring the axial force generated by the user on the handle 66 to the elongate body 20, such as by decoupling the shaft 48 from the push button 68 (for example, to allow free movement of the shaft 48 with respect to the handle 66 and elongate body 20) causes the elongate body 20 to push against the rear of the balloon 18 and, as a result, increase the outer diameter of the balloon 18. This increase in outer diameter prevents the balloon 18 from traveling into the vessel 111 to an undesired depth. Further, occlusion of the vessel by the highly conformable balloon 18 shown in FIG. 24 provides nearly the same result as occlusion of a vessel by a currently known balloon 96 that is not highly conformable. Therefore, the user retains the benefits discussed herein of using the highly conformable balloon 18 to perform the medical procedure without the potential for patient injury currently expected when using balloons inflated to a low pressure.

Figure 27:
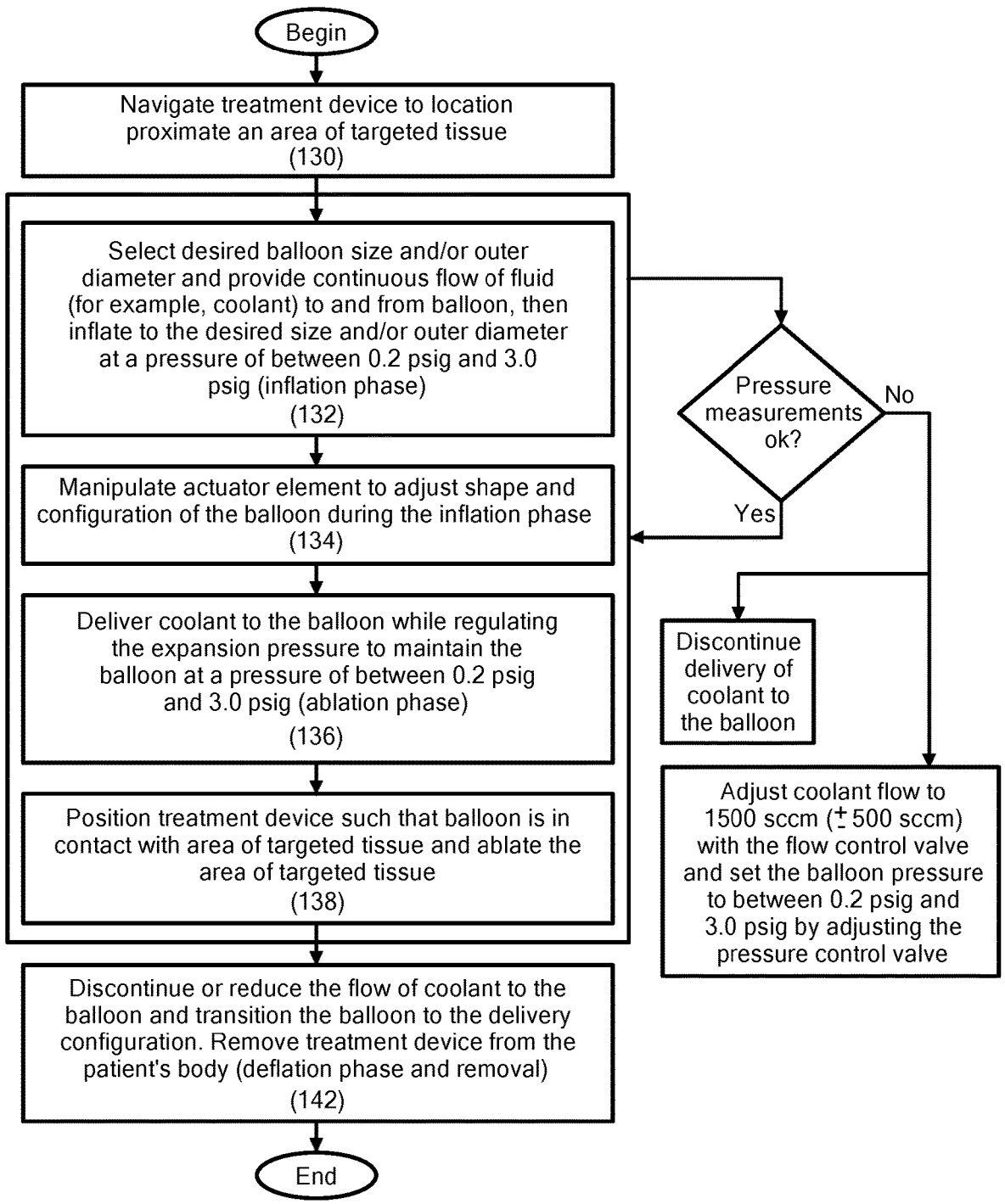
FIG. 27 shows a flow chart of an exemplary method for performing a medical procedure using a treatment device with a highly conformable balloon.

Referring now to FIG. 27, an exemplary method of using a medical system 10 including a treatment device 12 with a highly conformable balloon 18 is shown. In an exemplary first step 130, the user navigates the treatment device 12 to a location proximate an area of targeted tissue 108. In one embodiment, the area of targeted tissue 108 may be a pulmonary vein ostium, a location on the left atrial wall, or any other suitable location within the patient's body. The control unit 14 (for example, the processing circuitry 82) is then used to automatically, semi-automatically, and/or manually control inflation and use of the balloon 18 to perform an ablation procedure. For example, in an exemplary second step 132, the user selects a desired size and/or outer diameter of the balloon 18 using a touch-screen display 80 and/or other user input device of the medical system 10. Then, commencing the inflation phase, the control unit 14 manipulates or otherwise controls the flow control valve 86 in the fluid delivery conduit 42, the pressure control valve 88 in the fluid return conduit 46, and/or other valves in the fluid flow pathway(s) of the medical system 10 to provide a continuous flow of fluid to and from the balloon 18 to inflate the balloon 18 to the desired size and/or outer diameter (for example, to an outer diameter selected by the user). In one embodiment, the control unit 14 manipulates flow control valve 86 to adjust or control the flow, delivery, and circulation of the coolant to and within the balloon 18 when the treatment device 12 is communication with the control unit 14 and the control unit 14 manipulates pressure control valve 88 to control the pressure of expansion in the balloon 18 as measured by the Pitot tube 74 (or other pressure sensor) in the balloon 18. Optionally, if a currently known treatment device is in communication with the control unit 14, the control unit 14 may be configured to manipulate the flow control valve 86 to control the vacuum level based on a pressure measured at PT5 (shown in FIG. 5) to reproduce the vacuum level of previous control unit generation(s). In an exemplary third step 134, the user may also manipulate the push button 68 in the handle 66 to move the shaft 48 and adjust the shape and configuration of the balloon 18 during the inflation phase. For example, the shaft 48 may be advanced in a proximal-to-distal direction to elongate the balloon 18 (such as to create linear lesions) or the shaft 48 may be retracted in a distal-to-proximal direction to transition the balloon 18 into an at least substantially toroidal configuration (such as to create spot lesions or ablate rotors). However, it will be understood that the user may instead not engage the push button 68 and, instead, the shaft 48 may be allowed free movement within the elongate body 20 during the inflation phase (for example, when performing a pulmonary vein isolation procedure). In one embodiment, the balloon 18 is in fluid communication with the vacuum pump or vacuum source 84, and is inflated at a constant inflation pressure of between 0.2 psig and 3.0 psig. In one embodiment, the balloon 18 is inflated using coolant delivered to the interior chamber 60 at a flow rate of approximately 1500 sccm (±500 sccm). For example, the coolant flow may be adjusted to 1500 sccm (±500 sccm) with the flow control valve 86 and the balloon 18 pressure may be set to between 0.2 psig and 3.0 psig by adjusting the pressure control valve 88. Alternatively, a fixed amount of coolant may be delivered to the balloon 18 to increase the pressure within the balloon 18 to a target or desired pressure, such as by automatic, semi-automatic, or manual manipulation of the flow control valve 86, and the pressure control valve 88 may be manipulated (for example, automatically or semi-automatically by the control unit 14, or manually by the user) to help maintain or stabilize the pressure within the balloon at the target pressure. In one embodiment, once the target balloon pressure is achieved, the control valves 86, 88 may be closed (for example, automatically or semi-automatically by the control unit 14, or manually by the user) to stop the flow of coolant to and from the balloon 18.

Once the balloon 18 is inflated and in a desired configuration, the control unit 14 automatically or semi-automatically initiate the ablation phase and regulate the control valves 86, 88 (and/or the user may manually regulate the control valves 86, 88) in an exemplary fourth step 136 to maintain the balloon 18 at a relatively low ablation pressure. In one embodiment, the control unit 14 determines that the balloon 18 has reached the desired inflation size based on pressure measurements from the pressure sensor(s) 70, 72 and automatically initiate ablation phase. In another embodiment, the control unit 14 determines that the balloon 18 has reached the desired inflation size based on pressure measurements from the pressure sensor(s) 70, 72 and prompts the user to confirm and manually initiate the ablation phase. Once the ablation phase is initiated, no further adjustments to the size, shape, and/or configuration of the balloon 18 may be permitted. In one embodiment, the control unit 14 (for example, the processing circuitry 82 includes software with which the user may interact to lock, or prevent further modifications to, the balloon size, shape, and/or configuration.

In an exemplary fifth step 138, the user may position the treatment device 12 such that the balloon 18 is in contact with the area of targeted tissue. In one embodiment, the balloon 18 is used to ablate tissue with a constant pressure of between 0.2 psig and 3.0 psig, the same pressure as the inflation pressure, which is in contrast to a required inflation pressure of approximately 17.5 psig in currently known devices. This relatively low pressure allows the balloon 18 to be highly conformable and very flexible during use. In one embodiment, the balloon 18 is used to perform a pulmonary vein isolation and axial force exerted by the user at the handle 66 to enhance contact tissue contact with, and occlusion by, the balloon 18, is transferred through the elongate body 20. This, in turn, exerts an axial force on the rear of the balloon 18 and increases the balloon outer diameter, which prevents the balloon 18 from traveling too deeply into the pulmonary vein. Although positioning the balloon 18 to be in contact with the area of targeted tissue is described as being the fifth step 138, it will be understood that this step may occur before, during, or after the inflation phase.

Further, in an exemplary sixth step 140, the control unit 14 may continuously monitor pressure measurements from the pressure sensor(s) 70, 72 during the inflation phase and the ablation phase in a feedback loop to ensure the balloon 18 remains at the predetermined size, shape, and/or configuration, that the balloon 18 does not become over-pressurized, and/or to monitor a push force exerted on the handle 66 and/or elongate body 20 during use. If the control unit 14 determines adjustment in the coolant flow and/or balloon pressure is required (for example, based on the user's initial balloon size specifications), the control unit 14 automatically adjusts the control valve(s) 86, 88, vacuum pump or vacuum source 84, and/or other system components 10 as necessary to bring balloon 18 pressure back to within the range of 0.2 psig to 3.0 psig. Alternatively, the control unit 14 and/or the user may discontinue the delivery of coolant to the balloon 18 if the pressure measurements indicate a system and/or balloon failure. As the balloon is inflated and used to ablate an area of targeted tissue while the balloon 18 is in communication with the vacuum pump or vacuum source 84 (that is, while the balloon 18 is under a vacuum), the flow rate of the coolant used to cool the balloon 18 and the balloon pressure may be controlled independently by the control unit 14. Put another way, the control unit 14 may maintain the balloon at a pressure of between 0.2 psig and 3.0 psig, regardless of the flow rate of coolant within the balloon 18. However, flow rate may be adjusted. For example, when the balloon 18 is in the elongated third configuration (as shown in FIGS. 18-20), a lower coolant flow rate may be needed or desired than when the balloon 18 is in an expanded configuration (for example, as shown in FIGS. 10-17). In one embodiment, the flow rate may be adjusted or determined automatically or semi-automatically by the control unit 14 based on the selected inflation pressure of the balloon 18. Although monitoring pressure measurements is described as being the sixth step 140, it will be understood that this step may occur at any time during the procedure, in discrete steps or continuously throughout the procedure (for example, as shown in FIG. 27).

In an exemplary seventh step 142, the deflation phase is initiated (for example, the flow of coolant is discontinued or reduced) and the balloon 18 is transitioned to the delivery configuration for safe removal from the patient's body. Optionally, the balloon 18 may be allowed to thaw prior to removal to prevent injury when removing a balloon that is cryoadhered to the area of target tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:
1. A system for ablating tissue, the system comprising:
 a treatment device including:
  a balloon;
  an elongate body having a proximal portion, a distal portion, and at least one lumen;
  a shaft slidably disposed within the elongate body;

a handle, the handle being fixedly coupled to the proximal portion of the elongate body; and
a push button being in mechanical communication with the shaft, the push button being movable to a first position where the push button is depressed and a second position where the push button is released, movement of the push button to the first position exerts a force on the shaft and movement of the push button to the second position releases the force on the shaft so the shaft is freely movable with respect to the handle and the elongate body and causes the balloon to inflate,
a control unit including a fluid supply reservoir in fluid communication with the balloon and a pressure sensor, the control unit being configured to deliver fluid from the fluid supply reservoir to the balloon.

2. The system of claim 1, wherein the control unit is configured to maintain a balloon pressure between 0.2 psig and 3.0 psig during inflation of the balloon.

3. The system of claim 1, wherein the control unit is configured to maintain a balloon pressure between 0.2 psig and 3.0 psig during ablation of tissue.

4. The system of claim 1, further comprising:
a vacuum source;
a fluid delivery conduit between the fluid supply reservoir and the balloon; and
a fluid return conduit being disposed between the balloon and the vacuum source.

5. The system of claim 4, further comprising:
a flow control valve in fluid communication with the fluid delivery conduit; and
a pressure control valve in fluid communication with the fluid return conduit,
the control unit being configured to selectively adjust the flow control valve and the pressure control valve to maintain a balloon pressure between 0.2 psig and 3.0 psig.

6. The system of claim 1, wherein the control unit is configured to determine a balloon pressure based on a pressure measurement recorded by the pressure sensor.

7. The system of claim 6, wherein the control unit is configured to determine a static pressure within the balloon based on a recorded stagnation pressure within the balloon.

8. The system of claim 1, wherein the pressure sensor is configured to record pressure signals generated by a heartbeat, the control unit being configured to determine an occlusion status of the balloon based on the pressure signals recorded by the pressure sensor.

9. The system of claim 1, wherein the balloon has:
a proximal neck coupled to the distal portion of the elongate body; and
a distal neck coupled to the distal portion of the shaft, movement of the push button to the first position transitions the balloon between a first configuration and a second configuration and movement of the push button to the second position transitions the balloon between the first configuration and a third configuration.

10. The system of claim 9, wherein the first configuration is an at least substantially round configuration.

11. The system of claim 10, wherein the balloon is inflatable to a first outer diameter when in the first configuration and is further inflatable to a second outer diameter when in the first configuration.

12. The system of claim 11, wherein the first outer diameter is approximately 23 mm and the second outer diameter is approximately 36 mm.

13. The system of claim 9, wherein the second configuration is a toroidal configuration.

14. The system of claim 9, wherein the third configuration is an elongated configuration.

15. A system for ablating tissue, the system comprising:
a treatment device including:
an elongate body having a distal portion, a proximal portion, at least one lumen, and a pressure sensor,
a shaft slidably disposed within the elongate body, the shaft having a proximal portion and a distal portion;
a balloon having a distal neck and a proximal neck, the distal neck being coupled to the distal portion of the shaft and the proximal neck being coupled to the distal portion of the elongate body;
a handle, the handle being fixedly coupled to the proximal portion of the elongate body; and
a push button being in mechanical communication with the shaft, the push button being movable to a first position where the push button is depressed and a second position where the push button is released, movement of the push button to the first position exerts a force on the shaft and movement of the push button to the second position releases the force on the shaft so the shaft is freely movable with respect to the handle and the elongate body and causes the balloon to inflate,
a control unit including:
processing circuitry;
a coolant supply reservoir, in fluid communication with the balloon;
a pressure sensor that is in fluid communication with the coolant supply reservoir; and
a vacuum source;
a fluid delivery conduit between the coolant supply reservoir and the balloon; and
a fluid return conduit between the balloon and the vacuum source,
the processing circuitry being configured to adjust a flow of coolant through the fluid delivery conduit and the fluid return conduit to maintain the balloon at a balloon pressure of between 0.2 psig and 3.0 psig during both an inflation phase and an ablation phase, the processing circuitry being further configured to control the balloon pressure independently of a flow rate of coolant from the coolant supply reservoir.

16. The system of claim 15, further comprising:
a flow control valve in fluid communication with the fluid delivery conduit; and
a pressure control valve in fluid communication with the fluid return conduit,
the processing circuitry being configured to control the flow control valve and the pressure control valve and the vacuum source to maintain the balloon pressure at between 0.2 psig and 3.0 psig.

17. The system of claim 15, wherein the pressure sensor in the elongate body is configured to record pressure signals generated by a heartbeat, the control unit being configured to determine an occlusion status of the balloon based on the pressure signals recorded by the pressure sensor in the elongate body.

18. The system of claim 15, wherein the control unit is configured to determine the balloon pressure based on a pressure measurement recorded by the pressure sensor in the elongate body.

19. A method of performing a medical procedure, the method comprising:
- selecting a desired inflated size of a balloon of a treatment device;
- delivering a fluid to the balloon and withdrawing coolant from the balloon such that the balloon is inflated to the desired inflated size and has a pressure of between 0.2 psig and 3.0 psig;
- delivering a coolant to the balloon at a flow rate and maintaining the balloon at the pressure of between 0.2 psig and 3.0 psig, the pressure being controlled independently of the flow rate of the coolant, delivery of the coolant to the balloon reducing a temperature of the balloon to a temperature sufficient to cryoablate tissue;
- manipulating a push button in a handle of the treatment device to move a shaft in a proximal direction and a distal direction opposite the proximal direction while coolant is being delivered to the balloon, movement of the shaft to advance the shaft in a proximal-to-distal direction being configured to elongate the balloon and retraction of the shaft in a distal-to-proximal direction being configured to transition the balloon to a substantially toroidal configuration;
- positioning the treatment device such that the balloon is in contact with an area of targeted tissue;
- determining whether the balloon has reached the desired inflated size based on at least one pressure measurement received from at least one pressure sensor disposed within the balloon; and
- cryoablating the area of targeted tissue with the balloon once it is determined that the balloon has reached the desired inflated size with a constant pressure of between 0.2 psig and 3.0 psig.

20. The method of claim 19, further comprising:
- continuously monitoring a pressure within the balloon; and
- adjusting a flow of the coolant to the balloon and from the balloon by adjusting at least one of a flow control valve and a pressure control valve, adjusting the at least one of the flow control valve and the pressure control valve being independent of adjusting the flow rate of the coolant.

* * * * *